United States Patent [19]

Keith et al.

[11] Patent Number: 4,801,704

[45] Date of Patent: Jan. 31, 1989

[54] METHYLENE PENAM AND DERIVATIVES THEREOF

[75] Inventors: Dennis D. Keith, Montclair; Chung-Chen Wei, Cedar Knolls; Manfred Weigele, North Caldwell, all of N.J.

[73] Assignee: Hoffman-La Roche Inc., Nutley, N.J.

[21] Appl. No.: 195,476

[22] Filed: May 16, 1988

Related U.S. Application Data

[63] Continuation of Ser. No. 855,967, Apr. 23, 1986, abandoned.

[30] Foreign Application Priority Data

Jun. 1, 1985 [EP] European Pat. Off. ....... 85.106769.4

[51] Int. Cl.[4] .................. C07D 499/00; C07D 499/46
[52] U.S. Cl. .................................... 540/312; 540/314; 540/335; 540/338; 540/339; 540/342
[58] Field of Search ............... 540/312, 314, 335, 338, 540/339, 342

[56] References Cited

U.S. PATENT DOCUMENTS

| | | | |
|---|---|---|---|
| 3,984,397 | 10/1976 | Kamiya et al. | 540/305 |
| 3,989,685 | 11/1976 | Tanida et al. | 540/313 |
| 4,058,521 | 11/1977 | Ueyo et al. | 540/315 |
| 4,081,443 | 3/1978 | Ueyo et al. | 540/313 |
| 4,385,176 | 5/1983 | Kamiya et al. | 540/314 X |
| 4,447,602 | 5/1984 | Firestone et al. | 540/314 X |
| 4,451,399 | 5/1984 | Yasuda et al. | 540/312 X |

OTHER PUBLICATIONS

Journal of the American Chemical Society, pp. 5020 and 5021, Aug. 20, 1975.
Tetrahedron Letters, vol. 23, No. 29, 1982, pp. 2991–2994.

Primary Examiner—Werren B. Lone
Assistant Examiner—Vera C. Clarke
Attorney, Agent, or Firm—Jon S. Saxe; Bernard S. Leon; Matthew Boxer

[57] ABSTRACT

There are presented compounds of the formula

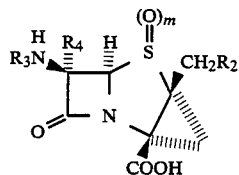

wherein $R_2$, $R_3$, $R_4$ and m are as described herein.

43 Claims, No Drawings

METHYLENE PENAM AND DERIVATIVES THEREOF

This application is a continuation of application Ser. No. 855,967, filed Apr. 23, 1986, now abandoned.

BACKGROUND OF THE INVENTION

The present invention relates to (2,3)-α-methylene penam and derivatives thereof. More particularly, the present invention relates to penam derivatives wherein the cyclopropyl group fused to the thiazolidine ring is on the opposite side of the molecule relative to the carboxylic acid, "R₃NH" and "R₂" substituent on the beta lactam or penam nuclei.

More specifically, and in an absolute sense, the bridgehead carbon atom located at the 4/5 ring fusion of these new penams has the R absolute configuration (Cahn-Ingold-Prelog method of designating absolute configuration). If the hydrogen atom substituent of this bridgehead carbon atom is designated as extending from the α-face of the molecule, then the cyclopropylmethylene also extends from the α-face. The carboxylic acid, "R₃NH" and "R₂" substituents are all on the β-face of the molecule. It should be noted that in this special arrangement, the absolute configuration of the carbon atom bearing the carboxylic acid substituent is opposite to all known penam antibacterials.

2,3-Lower alkyl alkylene penam-3-carboxylic acid derivatives wherein the fused cyclopropyl group is set forth without any stereochemical configuration are broadly disclosed in U.S. Pat. No. 3,904,607 to Kamiya et al. issued Sept. 9, 1975. An analysis of the disclosure indicates that the compounds produced have the fused cyclopropyl group on the β-face of the molecule (with the bridgehead carbon atom located on the 4/5 ring fusion having the R absolute configuration as noted above). Such compounds do not have the level and spectrum of antimicrobial activity of the present compounds.

Similar compounds have also been disclosed in U.S. Pat. No. 4,393,003 to Keith et al. issued July 12, 1983 but as noted above these compounds have the cyclopropyl fused ring in the β-position as stereochemically depicted in the Patent. Again the spectrum and activity levels are inferior to the present compounds.

A further article by Keith et al. in Tetrahedron Letters, 39(15), pages 2445–2458, 1983 discusses the mechanisms of action due to conformational differences in penam nuclei and their effect on penicillin antibacterial activity. Such disclosure does not include compounds wherein the methylene of the cyclopropyl group is in a "down" or α-configuration and the carboxylic acid is in an opposite "unnatural" absolute configuration.

DESCRIPTION OF THE INVENTION

This invention relates to a novel family of antibacterial penam derivatives, synthetic methods and intermediates useful in the production of such derivatives and the use of such derivatives as antibacterial agents.

The novel penam derivatives encompass compounds of the formula

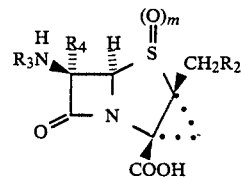

wherein R₂ is selected from the group consisting of hydrogen, lower alkyl, lower alkoxy, lower alkylthio, halo, hydroxy, cyano, trihalomethyl, azido, arylthio, five or six-membered substituted or unsubstituted heterocyclic thio, a five or six-membered heterocycle, and

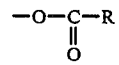

wherein R is hydrogen, lower alkyl, aryl, substituted aryl or substituted alkyl; R₃ is selected from the group consisting of hydrogen, an acyl group, a group of the formula

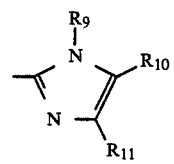

a group of the formula

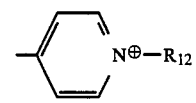

and a group (wherein another substituent is not present in the nitrogen at the 7-position) of the formula

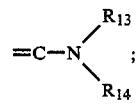

R₄ is selected from the group consisting of hydrogen, lower alkoxy, amino, lower alkylthio and amido; R₁₀ and R₁₁ are selected from the group consisting of hydrogen, halogen, cyano, hydroxy, carboxy, pyridyl, lower alkyl, aminoloweralkyl, hydroxyloweralkyl, C₂ to C₆ alkoxycarbonyl, lower alkyl amino lower alkyl, dilower alkyl amino lower alkyl, phenyl and substituted phenyl; R₉ is selected from the group consisting of hydrogen, hydroxy, amino, lower alkyl, lower alkanoyl, lower alkoxy, lower alkanoylamino, lower alkyl amino, phenyl lower alkyl phenyl and substituted phenyl; R₁₂ is selected from the group consisting of lower alkyl, substituted lower alkyl and aralkyl; R₁₃ and R₁₄ are selected from the group consisting of lower alkyl, halo-lower alkyl, hydroxy-lower alkyl, lower alkoxy-lower alkyl, carbalkoxylower alkyl, cyano lower alkyl, carbonyl lower alkyl, allyl, phenyl, substituted phenyl and cyclolower alkyl or R₁₃ and R₁₄ together with the nitrogen to which they are attached form a saturated substituted or unsubstituted heterocyclic ring having from 4 to 8 carbon atoms which may optionally contain one or two hetero atoms in place of a carbon atom and m is 0, 1 or 2 and the readily hydrolysable esters or salts of these compounds and hydrates of the compounds of formula I or of their esters or salts.

As used in this specification, the term "lower alkyl" or "alkyl" refers to both straight and branched chain saturated hydrocarbon groups having 1 to 8 and preferably, 1 to 4 carbon atoms, for example, methyl, ethyl, propyl, isopropyl, tertiary butyl and the like.

As used herein, the term "lower alkoxy" refers to a straight or branched chain hydrocarbonoxy group wherein the "alkyl" portion is a lower alkyl group as defined hereinbefore. Exemplary are methoxy, ethoxy, propoxy and the like.

The term "halo", "HAL" or "halogen" as used herein represents all four forms thereof, i.e. chloro, bromo, iodo or fluoro unless otherwise specified.

The term "acyl", as used in conjunction with $R^3$ herein, means and includes all organic radicals derived from an organic acid (i.e., a carboxylic acid) by removal of the hydroxyl group. Although the group $R^3$ may be any one of many acyl radicals, certain acyl groups are preferred.

Exemplary acyl groups are those acyl groups which have been used in the past to acylate β-lactam antibiotics including 6-aminopenicillanic acid and derivatives and 7-aminocephalosporanic acid and derivatives; see, for example, Cephalosporins and Penicillins, edited by Flynn, Academic Press (1972), Belgian Pat. No. 866,038 published Oct. 17, 1978, Belgian Pat. No. 867,994, published Dec. 11, 1978, U.S. Pat. No. 4,152,432, issued May 1, 1979, U.S. Pat. No. 3,971,778, issued July 27, 1976, and U.S. Pat. No. 4,173,199, issued Oct. 23, 1979. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R^5$ is alkyl, cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

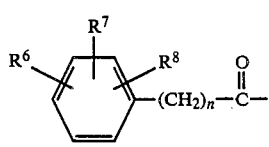

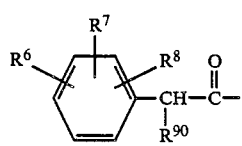

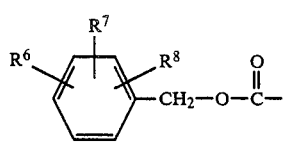

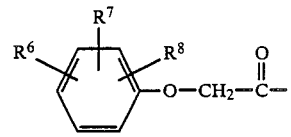

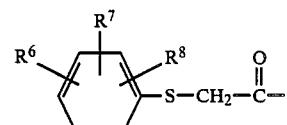

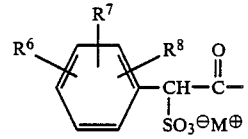

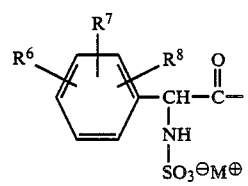

wherein n is 0, 1, 2 or 3; $R^6$, $R^7$, and $R^8$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R^{90}$ is amino, acylamino, hydroxyl, a carboxyl salt, protected carboxy, such as benzyloxycarbonyl, formyloxy or azido.

Preferred carbocyclic aromatic acyl groups include those having the formula

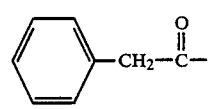

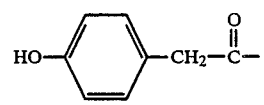

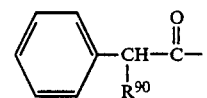

and

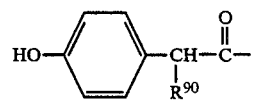

($R^{90}$ is preferably an amino group, a hydroxy group, or a carboxyl salt or sulfo salt)

Examples of other acyl groups of the formula

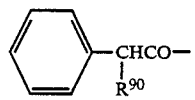

suitable for the purposes of the present invention are α-sulfophenylacetyl, α-hydroxysulfonyloxyphenylacetyl,
α-sulfamoylphenylacetyl,
α-(phenoxycarbonyl)phenylacetyl,
O-(p-tolyloxycarbonyl)phenylacetyl,
α-formyloxyphenylacetyl, α-carboxyphenylacetyl,
α-formylaminophenylacetyl,
α-benzyloxycarbonylphenylacetyl;
2-(N,N-dimethylsulfamoyl)-2-phenylacetyl,
2-bromo-2-thienylacetyl, etc.

(c) Heteroaromatic groups having the formula

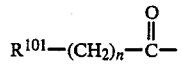

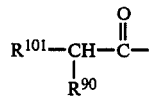

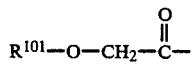

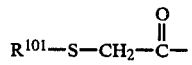

or

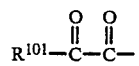

wherein n is 0, 1, 2 or 3; $R^{90}$ is as defined above; and $R^{101}$ is a substituted or unsubstituted 5-, 6- or 7-membered heterocyclic ring containing 1, 2, 3 or 4 (preferably 1 or 2) nitrogen, oxygen or sulfur atoms. Exemplary heterocyclic rings are thienyl, furyl, pyrrolyl, pyridinyl, pyrazinyl, thiazolyl, pyrimidinyl and tetrazolyl. Exemplary substituents are halogen, hydroxyl, nitro, amino, cyano, trifluoromethyl, alkyl of 1 to 4 carbon atoms, or alkoxy of 1 to 4 carbon atoms.

Preferred heteroaromatic acyl groups include those groups of the above formulas wherein $R^{101}$ is 2-amino-4-thiazolyl, 2-amino-5-halo-4-thiazolyl, 4-aminopyridin-2-yl, 2-amino-1,3,4-thiadiazol-5-yl, 2-thienyl, 2-furanyl, 4-pyridinyl or 2,6-dichloro-4-pyridinyl.

(d) [[(4-Substituted-2,3-dioxo-1-piperazinyl)carbonyl]-amino]arylacetyl groups having the formula

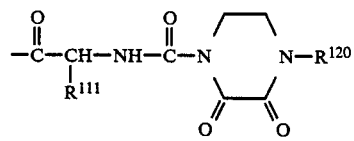

wherein $R^{111}$ is alkyl, hydroxyalkyl or an aromatic group (including carbocyclic aromatics such as those of the formula

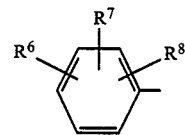

wherein $R^6$, $R^7$, and $R^8$ are as previously defined and heteroaromatics as included within the definition of $R^{101}$); and $R^{120}$ is alkyl, substituted alkyl (wherein the alkyl group is substituted with one or more halogen, cyano, nitro, amino or mercapto groups) e.g. 4-lower alkyl (preferably ethyl or methyl)-2,3-dioxo-1-piperazinecarbonyl-D-phenylglycyl.

(e) (Substituted oxyimino) arylacetyl groups having the formula

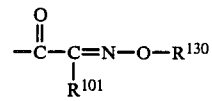

wherein $R^{101}$ is as defined above and $R^{130}$ is hydrogen, lower alkyl and $C_3$-$C_7$ cycloalkyl or substituted lower alkyl (wherein the alkyl group is substituted with 1 or more halogen, cyano, nitro, amino, mercapto, lower alkylthio, aromatic group (as defined by $R^{111}$), carboxyl (including salts thereof), amido, lower alkoxycarbonyl, phenylmethoxycarbonyl, diphenylmethoxycarbonyl, hydroxyalkoxyphosphinyl, dihydroxyphosphinyl, hydroxy (phenylmethoxy) phosphinyl, or diloweralkoxyphosphinyl substituents).

Examples of

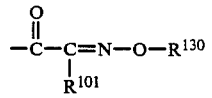

grouping are
2-[(2-chloroacetamidothiazol-4-yl)-2-[(p-nitrobenzyloxycarbonyl]methoxyimino]acetyl
2-(2-chloroacetamidothiazol-4-yl)-2-methoxyiminoacetyl,
2-(2-aminothiazol-4-yl)-2-isopropoxy-iminoacetyl,
2-(2-aminothiazol-4-yl)-2-methoxyiminoacetyl,
2-(2-aminothiazol-4-yl)-2-hydroxyiminoacetyl,
2-thienyl-2-methoxyiminoacetyl,
2-furyl-2-methoxyiminoacetyl,
2-(4-hydroxyphenyl)-2-methoxyiminoacetyl,
2-phenyl-2-methoxy-iminoacetyl,
2-phenyl-2-hydroxyiminoacetyl,
2-thienyl-2-hydroxyiminoacetyl,
2-thienyl-2-(dichloroacetyloxyimino)acetyl,
2-[4-(<<-D-glutamyloxy)phenyl]-2-hydroxyiminoacetyl,
2-[4-(3-amino-3-carboxypropoxy)phenyl-2-hydroxyiminoacetyl,
2-(5-chloro-2-chloroacetamidothiazol-4-yl)-2-methoxyiminoacetyl, 2-(5-chloro-2-aminothiazol-4-yl)-2-methoxyiminoacetyl, 2-[<<-(t-butoxycarbonyl)isopropoxyimino]-2-(2-sulfoamino-thiazol-4-yl)-acetyl,
2-[<<-(t-butoxycarbonyl)isopropoxyimino]-2-(2-triphenyl-methylamino-thiazol-4-yl)acetyl, 2-(2-chloroacetamidothiazol-4-yl)-2-isopropoxyiminoacetyl, 2-methoxyimino-2-(2-sulfoaminothiazol-4-yl)acetyl, 2-[(2-aminothiazol-4-yl)-2-carboxymethoxyimino]acetyl 2-[2-(2-mesylaminothiazol-4-yl)-2-isopropoxyiminoacetyl, 2-(2-imino-3-mesyl-4-thiazolin-4-yl)-2-isopropoxyiminoacetyl, 2-[(2-aminothiazol-4-yl)-2-(carboxyisopropoxyimino)acetyl etc.

(f) (Acylamino) arylacetyl groups having the formula

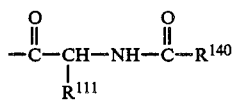

wherein $R^{111}$ is as defined above and $R^{140}$ is

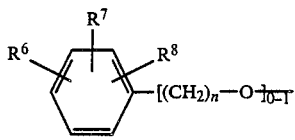

(where $R^6$, $R^7$, $R^8$ and n are as previously defined), hydrogen, lower alkyl, substituted lower alkyl, amino, alkylamino, (cyanoalkyl) amino, or acylamino.

Preferred (acylamino) arylacetyl groups of the above formula include those groups wherein $R^{140}$ is amino, or acylamino. Also preferred are those groups wherein $R^{111}$ is phenyl or 2-thienyl.

(g) [[[3-Substituted-2-oxo-1-imidazolidinyl]carbonyl]amino]arylacetyl groups having the formula

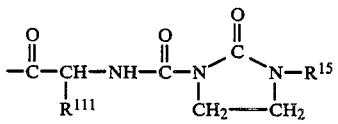

wherein $R^{111}$ is as defined above and $R^{15}$ is hydrogen, alkylsulfonyl, arylmethyleneamino (i.e., $-N=CH-R^{111}$ wherein $R^{111}$ is as defined above),

(wherein $R^{16}$ is hydrogen, alkyl or halogen substituted alkyl), aromatic group (as defined by $R^{111}$ above), alkyl or substituted alkyl (wherein the alkyl group is substituted with one or more halogen, cyano, nitro, amino or mercapto groups).

Preferred [[[3-substituted-2-oxo-1-imidazolidinyl]carbonyl]amino]arylacetyl groups of the above formula include those wherein $R^{111}$ is phenyl or 2-thienyl. Also preferred are those groups wherein $R^{15}$ is hydrogen, methylsulfonyl, phenylmethyleneamino or 2-furylmethyleneamino.

Especially preferred are compounds of the formula

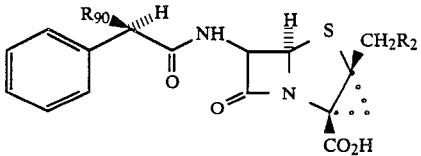

wherein $R_2$ is previously defined, and $R^{90}$ is hydrogen or hydroxy.

With regard to the "$R_2$" substituent, the terms "heterocycle" or "heterocyclic thio" refers to a saturated or unsaturated monocyclic or polycyclic heterocyclic group containing at least one heteroatom, such as, oxygen, sulfur or nitrogen.

The following fundamental ring systems may be mentioned as examples of the radical $R_2$: thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl and purinyl, as well as benzo-fused derivatives, for example benzoxazolyl, benzthiazolyl, benzimidazolyl and indolyl.

5-membered ring systems with a sulfur or oxygen atom and 1 to 3 nitrogen atoms, such as thiazolyl, in particular thiazol-2-yl and thiazol-2-yl N-oxide, thiadiazolyl, in particular 1:3,4-thiadiazol-5-yl and 1,2,4-thiadiazol-5-yl, oxazolyl, preferably oxazol-2-yl, and oxadiazolyl, such as 1,3,4-oxadiazol-5-yl, are preferred. Furthermore, 5-membered ring systems with 2 to 4 nitrogen atoms, such as imidazolyl, preferably imidazol-2-yl, triazolyl, preferably 1,3,4-triazol-5-yl and 1,2,3- and 1,2,4-triazol-5-yl, and tetrazolyl, preferably 1H-tetrazol-5-yl and 2H-tetrazolyl, are preferred. Benzofused derivatives, in particular benzoxazol-2-yl, benzthiazol-2-yl and benzimidazol-2-yl are also preferred.

Furthermore, other preferred ring systems are 6-membered ring systems with 1 to 3, preferably 1 to 2 nitrogen atoms, such as, for example, pyridyl, such as pyrid-2-yl, pyrid-3-yl and pyrid-4-yl, pyrimidyl, preferably pyrimid-2-yl and pyrimid-4-yl, triazinyl, preferably 1,3,4-triazin-2-yl and 1,3,5-triazin-4-yl, pyridazinyl, in particular pyridazin-3-yl, and pyrazinyl.

Where the radical "$R_2$" denotes a heterocyclic or heterocyclic thio radical it can be mono- or di-substituted by, for example, lower alkyl, lower alkenyl (e.g. vinyl, alkyl, butenyl, etc.), aryl (e.g. phenyl, tolyl, etc.), halo (e.g. chloro, bromo, fluoro or iodo), amino, oxo, hydroxy, lower alkoxy, trifluoromethyl, mercapto or carboxyl.

By the term "aryl" is meant a substituted or unsubstituted aromatic moiety, such as, phenyl, tolyl, xylyl, mesityl, cumanyl, naphthyl and the like wherein said aryl group may have 1 to 3 suitable substituents, such as, halo (fluoro, chloro, bromo, etc.), hydroxy and the like.

By the term "acyl" (as used for other than "$R^3$") or "lower alkanoyl" or "alkanoyl" as utilized herein is intended a moiety of the formula

wherein $R^{25}$ is $C_1$ to $C_6$ or hydrogen, e.g. acetyl, propionyl, butyryl and the like.

By the term "substituted phenyl" is meant phenyl mono- or di-substituted by substituents selected from the group consisting of halo(chloro, bromo, fluoro, etc.), lower alkyl, amino, nitro and trifluoromethyl.

By the term "substituted alkyl" or "substituted lower alkyl" is meant a "lower alkyl" moiety substituted by, for example, halo(chloro, fluoro, bromo, etc./trifluoromethyl, amino, cyano, etc.

By the term "lower alkenyl" is meant straight or branched chain hydrocarbon groups which contain an olefinic double bond having 2 to 6 carbon atoms i.e. the radical of compounds of the formula $C_nH_{2n}$ wherein n is 2 to 6 e.g. alkyl, vinyl etc.

By the term "aralkyl" is meant a hydrocarbon group having both aromatic and aliphatic structures, that is, a hydrocarbon group in which a lower alkyl hydrogen atom is substituted by a monocyclic aryl group. e.g. phenyl, tolyl, etc.

As noted previously the substituents $R_{13}$ and $R_{14}$ taken with the nitrogen to which they are attached may form a 4 to 8 membered heterocyclic ring which may optionally be interrupted by heteroatoms, such as, oxygen, sulfur or nitrogen, such as, for example, morpholino, piperidino, piperazino, pyrrolidino, etc.

By the term "cycloloweralkyl" is meant a 3-6 membered saturated carbocyclic moiety, e.g. cyclopropyl, cyclobutyl, cyclohexyl, etc.

As readily hydrolyzable esters of the compounds of formula I there are to be understood compounds of formula I, the carboxy group(s) of which (i.e. the 2-carboxy group) is/are present in the form of readily hydrolyzable ester groups. Example of such esters, which can be of the conventional type, are the lower alkanoyloxyalkyl esters (e.g. the acetoxymethyl, pivaloyloxymethyl, 1-acetoxyethyl and 1-pivaloyloxyethyl ester), the lower alkoxycarbonyloxyalkyl esters (e.g. the methoxycarbonyloxymethyl), 1-ethoxycarbonyloxyethyl and 1-isopropoxycarbonyloxyethyl ester), the lactonyl esters (e.g. the phthalidyl and thiophthalidyl ester), the lower alkoxymethyl esters (e.g. the methoxymethyl ester) and the lower alkanoylaminomethyl esters (e.g. the acetamidomethyl ester). Other esters (e.g. the benzyl and cyanomethyl esters) can also be used.

Example of salts of the compounds of formula I are alkali metal salts such as the sodium and potassium salt, the ammonium salt, alkaline earth metal salts such as the calcium salt, salts with organic bases such as salts with amines (e.g. salts with N-ethyl-piperidine, procaine, dibenzylamino, N,N'-dibenzylethylenediamine, alkylamines or dialkylamines) as well as salts with amino acids such as, for example, salts with arginine or lysine. The salts can be mono-salts, di-salts or tri-salts.

The compounds of formula I also form addition salts with organic or inorganic acids. Examples of such salts are hydrohalides (e.g. hydrochlorides, hydrobromides and hydroiodides) as well as other mineral acid salts such as sulphates, nitrates, phosphate and the like, alkyl sulphonates and monoarylsulphonates such as ethanesulphonates, toluenesulphonates, benzenesulphonates and the like and also other organic acid salts such as acetates, tartrates, maleates, citrates, benzoates, salicylates, ascorbates and the like.

The compounds of formula I as well as their salts and readily hydrolyzable esters can be hydrated. The hydration can be effected in the course of the manufacturing process or can occur gradually as a result of hygroscopic properties of an initially anhydrous product.

(2,3)-α-methylene penam and derivatives thereof according to the invention have activity against a broad range of both gram-negative and gram-positive bacteria.

(2,3)-α-methylene penam and derivatives thereof can be used as agents to combat bacterial infections (including urinary tract infections and respiratory infections) in mammalian species, e.g. dogs, cats, horses, etc., and humans.

The in vitro activity of (2,3)-α-methylene penam as measured by the Minimum Inhibitory Concentration in micrograms/ml (MIC-ug/ml.) utilizing the Agar Well Diffusion Method against a variety of Gram-positive and Gram-negative organisms is as follows:

| Organism | [2R-(2α,4α,6β,7α)]-4-methyl-8-oxo-7-[(phenylacetyl)amino]-5-thia-1-azatricyclo[4.2.0.0$^{2,4}$]octane-2-carboxylic acid potassium salt (End Product of Example 6) |
|---|---|
| Proteus vulgaris 101N | 7.8 |
| Escherichia coli 94 | 15.7 |
| Klebsiella pneumoniae 369 | 15.7 |
| Staphylococcus aureus 82 | 0.23 |
| Staphylococcus aureus 1059B | 1.9 |
| Micrococcus lutens PCI | 0.45 |
| Bacillus megaterium 164 | 0.9 |
| Bacillus sp E | 1.9 |
| Bacillus subtilis 558 | 0.12 |
| Bacillus sp TA | 0.12 |

| Organism | 5R-2-Methyl-6β-(2-thienyl)-acetacetyl-amino-(2,3)-α-methylenepenam-3-carboxylate Potassium Salt (End Product of Example 17) |
|---|---|
| Proteus vulgaris 101N | >500 |
| Escherichia coli 94 | 15.6 |
| Klebsiella pneumoniae 369 | 15.6 |
| Staphylococcus aureus 82 | 0.49 |
| Staphylococcus aureus 1059B | 1.95 |
| Micrococcus lutens PCI | 0.98 |
| Bacillus megaterium 164 | 1.95 |
| Bacillus sp E | 3.9 |
| Bacillus subtilis 558 | 0.24 |
| Bacillus sp TA | 0.24 |

| Organism | [2R-[2α,4α,6β,7α(R*)]]-7-[(Phenylhydroxyacetyl)amine]-4-methyl-8-oxo-5-thia-1-azatricyclo[4.2.0.0./2,4/octane-2-carboxylic acid, sodium salt (End Product of Example 23) |
|---|---|
| Proteus vulgaris 101N | 7.8 |
| Escherichia coli 94 | 7.8 |
| Klebsiella pneumoniae 369 | 7.8 |
| Staphylococcus aureus 82 | 0.24 |
| Staphylococcus aureus 1059B | 1.95 |
| Micrococcus lutens PCI | 0.49 |
| Bacillus megaterium 164 | 0.98 |
| Bacillus sp E | 15.6 |
| Bacillus subtilis 558 | 0.24 |
| Bacillus sp TA | 0.24 |

For combating bacterial infections in mammals a compound of this invention can be administered to a mammal in need thereof in an amount of about 5 mg/kg/day to about 250 mg/kg/day, preferably about 10 mg/kg/day to about 20 mg/kg/day. All modes of administration which have been used in the past to deliver penicillins and cephalosporins to the site of the infection are also contemplated for use with the novel family of (2,3)-α-methylene penam or its derivatives of this invention. Such methods of administration include oral, intravenous, intramuscular and as a suppository.

The following reaction schemes set forth the methods and intermediates useful in producing the novel end products of formula I.

In the following reaction sequences where a substituent group is present which may be attacked during the reaction it should be in protected form utilizing well known protecting groups. For example amino groups may be protected with easily removable protective groups employed in peptide chemistry, such as an alkylcarbonyl group such as formyl, acetyl, propionyl, etc., an alkoxycarbonyl group such as t-butoxycarbonyl, etc., an alkoxyalkylcarbonyl group such as methoxyacetyl, methoxypropionyl, etc., a substituted alkoxycarbonyl group such as trichloroethoxycarbonyl, etc., a substituted alkylcarbonyl such as monochloromethylcarbonyl, monochloroethylcarbonyl, dichloromethylcarbonyl, dichloroethylcarbonyl, trichloromethylcarbonyl, trichloroethylcarbonyl, trichloropropylcarbonyl, etc., an aralkyloxycarbonyl group such as benzyloxycarbonyl, etc., a substituted aralkyloxycarbonyl group such as p-nitrobenzyloxycarbonyl, etc. or amino group protected with proton.

Preferred protecting groups include benzyloxycarbonyl (CBZ) or tert.-butyloxycarbonyl (t-BOC) or a silyl protecting group, e.g. trimethylsilyl.

As ester protecting group ($R_{65}$) one may utilize an ester form which can be easily converted into a free carboxyl group by mild treatment with an acid or alkali or by reduction, the ester protecting group being exemplified by, for example, beta-methylsulfonylethyl, trimethylsilyl, t-butyldimethylsilyl, benzhydryl, $\beta,\beta,\beta$-trichloroethyl, phenacyl, p-methoxybenzyl, p-nitrobenzyl, methoxymethyl, etc. After reaction sequences are complete the above groups may be removed as noted above.

The removal of the protecting group for the amino substituent may be conducted by acid treatment for t-butoxycarbonyl, etc. or by treatment with zinc and an acid for $\beta,\beta,\beta$-trichloroethoxycarbonyl etc. or by catalytic reduction for p-nitrobenzyloxycarbonyl, etc.

The following reaction schemes set forth novel methods and intermediates to produce the compound of claim 1.

Scheme 1

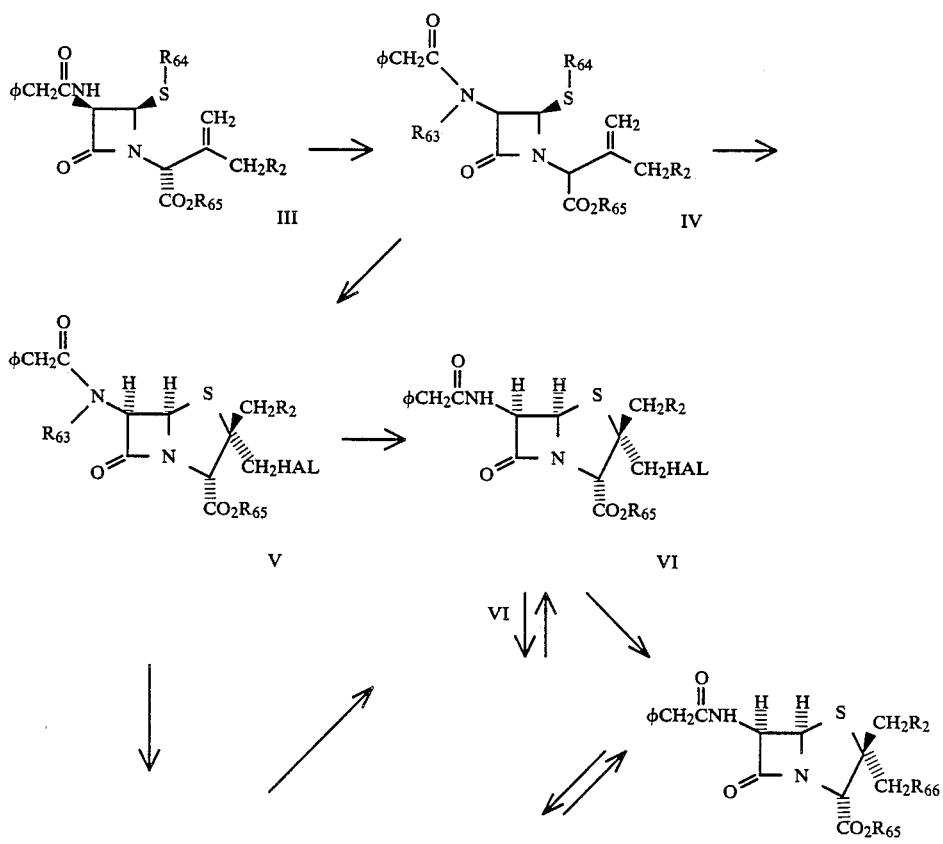

-continued
Scheme 1

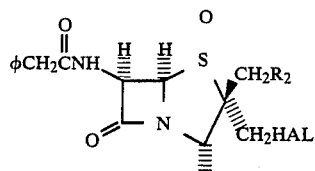
VII

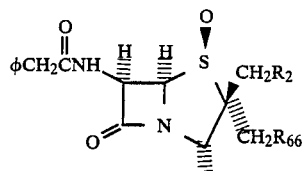
VIII wherein $R_{63}$ is acyl, e.g. trihalosubstituted acetyl; $R_{64}$ is selected from halogen, aryl NH—, aryl S—, alkyl S—, heterocyclicthio, Aryl O—, heterocyclicoxo, RCOS— or

wherein R is alkyl or aryl; $R_{65}$ is an ester protecting group and $R_{66}$ is a leaving group, such as halogen, triflate, mesylate, acetate, trifluoroacetate or tosylate and $R_2$ is as above, with the proviso that when $R_2$ and $R_{66}$ are both halogen they are different, and with the further proviso that HAL is a different and more easily displaced halogen than $R_{66}$ when $R_{66}$ is halogen. It should be noted that while these schemes are illustrated with a phenylacetamide substituent in the beta-lactam structure, the processes work equally well with a phenoxy acetamido substituent or other acylamino substituents (that is, protecting group) in the same position.

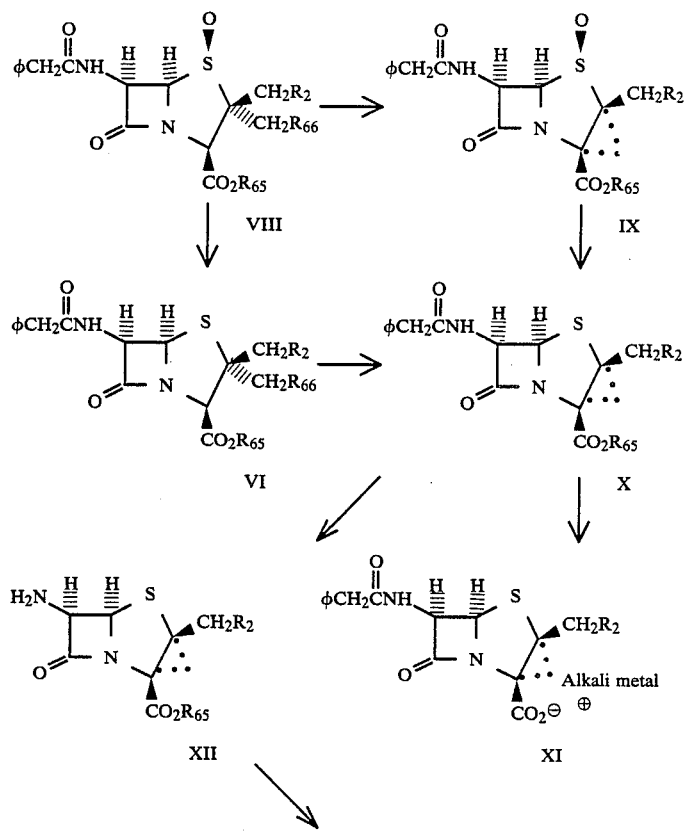

Scheme 2

Scheme 2
-continued

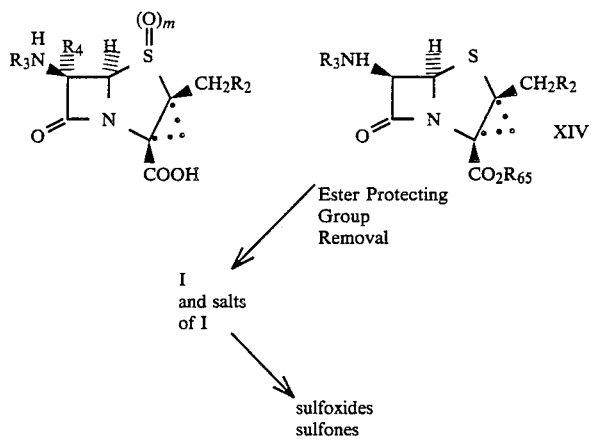

wherein $R_2$, $R_3$, $R_4$, $R_{65}$, $R_{66}$, and m are as described above.

III→IV

The compound of formula III is a known compound whose method of production is disclosed in Example 11 utilizing readily available materials known in the art.

The compound of formula III is reacted with a trihalosubstituted acetic anhydride, e.g. trichloro- or tribromoacetic anhydride preferably trifluoroacetic anhydride in a chlorinated hydrocarbon, e.g. chloroform or methylene chloride. The reaction is carried out at between about −20° C. to 50° C. with about room temperature as preferred.

IV→V

The compound of formula IV is thereafter halogenated with any halogenating agents, preferably brominated, utilizing bromine, in the presence of an inert base which functions as an acid scavenger. Suitable bases include calcium oxide or potassium carbonate. The reaction may be carried out between −20° C. to room temperature with about 0° C. as preferred.

V→VI

The compound of formula V is thereafter hydrolysed with aqueous base, such as, sodium bicarbonate, with hydrated silical gel or organic base such as aniline in aprotic solvent. The reaction temperature may be varied from about 0° C. to 50° C. with about room temperature as preferred.

VI→VI'

The halo (Hal) substituent of the compound of formula VI may thereafter be displaced with a chosen mesylate, tosylate, acetate or other halogen. The reaction is carried out with the alkali or alkaline earth metal salt of methane sulfonic acid, para-toluene sulfonic acid or acetic acid depending on the substituent desired. The reaction is carried out at between about −20° C. to room temperature with about room temperature preferred. An acid scavenger may be utilized as in step IV→V.

V→VII

The compound of formula V is thereafter oxidized to provide the S-oxide. The oxidation may be accomplished with a peracid such as m-chloroperbenzoic acid, peracetic acid or pertrifluoroacetic acid or with an alkali metal (Na or K) periodate. The reaction may be run in the presence of a halogenated hydrocarbon, such as, dichloroethane or methylene chloride. The reaction temperature may be varied from about −20° C. to 50° C. with about room temperature preferred. The oxidation may also be accomplished by ozonolysis under suitable conditions.

The oxidation product is thereafter subjected to hydrolysis with a base as in step V→VI.

VII→VI

The compound of formula VII thereafter may undergo a reduction with a suitable reducing agent, such as, a phosphorus trihalide, i.e. phosphorus trichloride or tribromide in dimethylformamide or sodium iodide and trifluoroacetic anhydride in acetone. The reduction is carried out at between about −20° C. and room temperature with about 0° C. as preferred.

VI or VI'→VIII

The compounds of formulas VI or VI' are thereafter oxidized with a peracid or periodate utilizing the same reactants and reaction conditions as set forth in step V→VII above.

VIII→VI or VI'

The compound of formula VIII may be reduced to provide the compounds of formulas VI or VI' by utilizing reactants and reaction conditions as set forth in step VII→VI or VI' above.

VIII→IX or VI→X

The compounds of formulas VIII or VI are converted to compounds of formulas IX or X by reaction with an organic amine base, preferably a tertiary amine base, such as, 1,4-diazabicyclo[2.2.2.]]octane, 1,8-diazabicyclo[5.4.0]undec-7-ene or 1,5-diazabicyclo[4.3.0]non-5-ene in a polar organic solvent, such as, dimethylformamide, dioxane or tetrahydrofuran. The reaction temperature may be varied from about −50° C. to 0° C. with about −10° C. as preferred.

Other reactants and reaction conditions which may be utilized to achieve cyclization are disclosed in U.S. Pat. No. 3,094,607 at column 23, said teaching being incorporated herein by reference.

IX→X

The compound of formula IX may thereafter be reduced to provide the compound of formula X utilizing the reactants and reaction conditions set forth in VII→VI or VI′ above.

X→XII

The compound of formula X is thereafter reacted with a phosphorus pentahalide, preferably, phosphorous pentachloride in a tertiary amine base, such as, pyridine. The reaction is carried out at a temperature in a range of from about −20° C. to 50° C. with about room temperature as preferred. Thereafter the intermediate product is treated with a $C_1$ to $C_4$ alkanol, such as, methanol or ethanol with n-propanol as preferred. Thereafter the reactants are subject to a hydrolysis utilizing the reactants and reaction conditions as set forth in V→VI above.

X→XI

The ester protecting group ($R_{65}$) may thereafter be removed by conventional means, e.g. hydrolysis, hydrogenolysis. When $R_{65}$ is R-nitrobenzyl, it is removed by a reduction utilizing palladium on carbon (charcoal) and hydrogen in various solvent systems with a two phase system of ethyl acetate/aqueous alkali metal (Na or K) bicarbonate or methanol/tetrahydrofuran followed by treatment with aqueous alkalimetal (Na or K) bicarbonate. The resultant material is chromatographed utilizing known techniques to isolate the alkali metal salt.

XII→XIV

The compound of formula XII is converted to the compound of formula XIV via any conventional technique for acylating and protecting an amino compound with a carboxylic acid from which $R_3$ is desirable or an active derivative thereof, such as, the corresponding acid halide, e.g. phenylmethoxy carbonyl chloride, acid anhydride, e.g. chloroacetic anhydride, or active ester in the presence of a base, e.g. alkali metal (Na or K) hydroxides, carbonates or bicarbonates or tertiaryamines, such as, triethylamine or pyridine. Suitable solvents include mixed solvents, such as, miscible solvents, e.g. tetrahydrofuran or acetone with water or immiscible solvents, such as, chloroform with water. Although the temperature is not critical the reaction generally proceeds between about 0° C. to 30° C. with about room temperature preferred.

The compounds of formula XIV may thereafter undergo removal of the ester protecting group following the reaction conditions set forth in step X→XI above. Thereafter the alkali metal salt may be reacted to form the acid by treatment with acid e.g., hydrochloric or sulfuric acid.

In order to manufacture the easily hydrolysable esters of the carboxylic acids of the formula I compound; the carboxylic acid is preferably reacted with the appropriate halide containing the ester group, preferably with the iodide. The reaction can be accelerated with the aid of a base, e.g. an alkali metal hydroxide or carbonate, or an organic amine, such as triethylamine. The esterification reaction is preferably carried out in an inert organic solvent, such as dimethylacetamide, hexamethylphosphoric acid bromide, dimethylsulphoxide or, preferably, dimethylformamide. The temperature is preferably in the range of about 0°–40° C.

The salts and hydrates of the compounds of the formula I, or the hydrates of these salts, can be manufactured in a manner known per se, e.g. by reacting the carboxylic acid of the formula I with an equivalant amount of the desired base, appropriately in a solvent, such as water or in an organic solvent, such as ethanol, methanol, acetone, and many others. The temperature of the salt formation is not critical, it is in general room temperature, but can also easily be above or below room temperature, for example in the range from 0° C. to +50° C.

The manufacture of the hydrates usually takes place automatically, in the course of manufacturing process or as a result of hygroscopic properties of an initially anhydrous product. For controlled manufacture of a hydrate, a completely or partially anhydrous (carboxylic acid of the formula I or ester or salt thereof) can be subjected to a moist atmosphere, e.g. at about "10° C. to +40° C.

In the following examples the stereochemical configurations are set forth in either alpha (or α) and beta (or β) in the written formulas.

EXAMPLE 1

[3R][1(R*),3-alpha,4-alpha]]-4-(benzothiazol-2-yldithio)-3-[(trifluoroacetyl)(phenylacetyl)amino]-alpha-(1-methyethenyl)-2-oxo-1-azetidineacetic acid (4-nitrophenyl)methyl ester 6.35 g of seco-penicillin i.e. [3R-[1(R*),3α,4α]]-4--(benzthiazol-2-yldithio)-α-(1-methylethenyl)-2-oxo-3-[[phenylacetyl)amino]-α-(1-methylethenyl)-2-oxo-3-[[phenylacetyl)amino]-1-azetidineacetic acid (4-nitrophenyl)methyl ester are taken up in 45 mL of $CHCl_3$ which had been dried over sieves and then passed through basic alumina. To this mixture was added 45 mL of cold trifluoroacetic anhydride. The mixture was stirred at room temperature and after about 40 minutes, the reaction solution became clear. The reaction mixture was concentrated. azeotroped twice with toluene and once with dry $CHCl_3$. The residue was dried in vacuo in a water bath with a temperature of 30°–35° C. to yield the desired end product. Analysis by nmr indicated a trace of starting material remained.

EXAMPLE 2

[2-S-(2α,3α,5α,6β)]- and [2S-(2α,3β,5α,6β)]-3-(bromomethyl)-3-methyl-6-[(trifluoroacetyl)(-phenylacetyl)amino]-7-oxo-4-thia-1-azabicyclo]3.2.0-]heptane-2-carboxylic acid (4-nitrophenyl)methyl ester The product of Example 1 i.e. the trifluoroacetyl seco-penicillin, was taken up in 40 mL of dry methylene chloride. Thereafter 1.12 g of calcium oxide was added to the reaction mixture and the mixture cooled to 0° C. A bromine solution (24.5 mL) was added dropwise over approximately ten minutes following completion of the addition. Thereafter a cold mixture of ether (120 mL)/petroleum ether (95 mL) was added and stirred for 10 minutes at 0°.

The reaction mixture was filtered through a bed of celite and the filtrate concentrated to yield a mixture of the α and β-bromomethylpenam imides named in the title to Example 2.

The crude product was used as is for Example 3, wherein the thiazolidine sulfide was oxidized to a sulfoxide. For reasons discussed in Example 3, it is likely that some of the very labile trifluoroacetyl phenylacetylimide was hydrolyzed during the work-up. Thus, the crude mixture described above also contains some imide hydrolysis product—i.e. the 6β-phenylacetylamide as well as the imide.

EXAMPLE 3

[2S-(2α,3β,4β,5α,6β)] and [2S-(2α,3α,4β,5α,6β)]-3-bromomethyl)-3-methyl-7-oxo-6-[(phenylacetyl)amino]-4-thia-1-azabicyclo[3.2.0]heptane-2-carboxylic acid (4-nitrophenyl)methyl ester 4-oxide and [2S-(2α,3β,4α,5α,6β)] and [2S-(2α,3α,4α,5α,6β)]-3-(bromomethyl)-3-methyl-7-oxo-6-[(phenylacetyl)amino]-4-thia-1-azabicyclo[3.2.0]heptane-2-carboxylic acid (4-nitrophenyl)methyl ester 4-oxide The mixture of α- and β-bromomethylpenams from Example 2 was taken up in 80 cc of methylene chloride. A small amount of material remained insoluble but was left in the mixture. The mixture was again cooled to 0° C. 1.93 g of m-chloroperbenzoic acid (85 percent pure) in 20 mL of methylene chloride was added dropwise over 5-10 minutes and the mixture stirred for one hour in the cold. The reaction mixture was worked up by extracting with 12.5° $Na_2SO_3$ (three times), water (one time) and brine (two times). The resultant organic phase was dried over $Na_2SO_4$ and concentrated and the residue dried in vacuo.

Thereafter the crude sulfoxide residue was chromatographed on silica gel using ethyl acetate/cyclohexane for elution. The four isomeric bromomethylpenam sulfoxides of the title (Example 3) were isolated from this chromatography. Structure assignment was made from their NMR spectra.

Normally, oxidation of penicillanic acids bearing a 6β-imide (e.g. phthalimide) yield the "α-sulfoxide", whereas oxidation of penicillanic acids with a secondary 6β-amide residue leads to the β-sulfoxides.* The isolation of both α- and β-sulfoxides from this reaction indicates some imide hydrolysis occurred in isolation of the products.
*R. D. G. Cooper and G. Koppel, Chemistry and Biology of β-Lactam Antibiotics (Edited by R. B. Morin and M. Gorman), Vol. 1, pp 3–17. Academic Press, New York (1982).

EXAMPLE 4

[2S-(2α,3α,5α,6β)]-3-(bromomethyl)-3-methyl-7-oxo-6-[(phenylacetyl)amino]-4-thia-1-azabicyclo[3.2.0]heptane-2-carboxylic acid (4-nitrophenyl)methyl ester 2.80 g of the α-bromomethylpenam α-sulfoxide of Example 3 were taken up in 75 mL of dry dimethylformamide and cooled to <0° C.

Phosphorus tribromide (1.75 mL) was added neat over approximately five minutes to the α-sulfoxide solution. The mixture was stirred for 25 minutes in the cold. The reaction mixture was poured into cold aqueous sodium bicarbonate (12.1 g in 590 mL of water). The mixture was extracted twice with 270 mL of ethyl acetate. The organic layers were combined and washed once with 200 mL of a water/brine mixture (1:1). The extract was then dried over sodium sulfate, concentrated and concentrated in vacuo to yield the α-bromomethyl sulfide.

EXAMPLE 5

[2R-(2α,4α,6β,7α)[-4-methyl-8-oxo-7-[(phenylacetyl)amino]-5-thia-1-azatricyclo[4.2.0.0$^{2,4}$]octane-2-carboxylic acid (4-nitrophenyl)methyl ester The end product of Example 4, was taken up in 45 mL of dry dimethylformamide and cooled in a −30° C. bath. Thereafter 0.78 mL of 1,8-diazabicyclo[5.4.0[undec-7-ene (DBU) in 40 mL of DMF was added to the mixture over an 8-9 minute period. The reaction mixture was stirred for 45 minutes at −30° C. The mixture was thereafter poured into 170 mL of cold 0.2N HCl. The mixture was extracted with 450 mL of ethyl acetate and the layers separated. The organic layer was extracted with an additional 170 mL of cold 0.2N HCl followed by 1% sodium bicarbonate (100 mL) and finally brine. The extract was dried over sodium sulfate, concentrated and dried in vacuo.

The crude material was dissolved in $CHCl_3$ and passed through a bed of silica gel in a sintered glass funnel. Fractions of approximately 100 mL were collected. Fractions 1-3 were combined, concentrated, and the material recrystallized from ethyl acetate. Some crystals came out upon cooling. Thereafter hexane was added and the solid material was isolated by filtration to yield the title compound as a crystalline solid: mp 135°-142° C.

EXAMPLE 6

[2R-(2α,4α,6β,7α)]-4-methyl-8-oxo-7-[(phenylacetyl)amino]-5-thia-1-azatricyclo[4.2.0.0$^{2,4}$]octane-2-carboxylic acid potassium salt The tricyclic p-nitrobenzyl ester end product of Example 5 (17.2 mg) was taken up in 2 mL of ethyl acetate. 2 mL of water was then added followed by 3.8 mg of potassium bicarbonate and finally the catalyst, i.e., 10% palladium on carbon. The reaction mixture was hydrogenated at room temperature for one (1) hour with vigorous stirring. The two phase system was filtered through a bed of celite to remove the catalyst. The two layers were separated. The aqueous phase was washed with ethyl acetate and the organic phase with water. The two layers were separated. The aqueous phase was washed with ethyl acetate and the organic phase with water. The two aqueous phases were combined and concentrated to remove residual ethyl acetate. The concentrated phases were filtered through a millipore filter to remove any catalyst which remained. The filtrate was freeze dried.

The filtrate including crude end product was dissolved in water and chromatographed using a sephadex column (Pharmacia, Sephadex G-25, 1 cm×25 cm). Fractions of approximately 2 mL were collected. The desired end product was found in fractions 9 and 10. Each was freeze-dried and the desired end product of the title was isolated as an amorphous solid. The structure was confirmed by NMR and IR.

EXAMPLE 7

[2R-(2α,4α,5α,6β,7α)]-4-methyl-8-oxo-7[(phenylacetyl)amino]-5-thia-1-azatricyclo[4.2.0.0$^{2,4}$]octane-2-carboxylic acid (4-nitrophenyl)methyl ester 3-oxide The α-bromomethylpenam β-sulfoxide (2.94 g), one of the products of Example 3, was taken up in 35 mL of dry DMF. The solution was cooled to between −35° C. to 40° C. and 0.81 mL of 1,8-diazabicyclo[5.4.0] undec-7-ene in 25 mL of DMF was added over a ten (10) minute period. An internal temperature of −35° to −40° C. was maintained throughout the addition. The mixture was stirred for 45 minutes in the cold.

The reaction mixture was poured into 120 mL of cold 0.2N HCl and extracted with 300 mL of ethyl acetate. The two layers which formed were separated. The organic phase was again extracted with an additional 120 mL of cold 0.2N HCl. This was followed by an extraction with 100 mL of cold 1° sodium bicarbonate and finally with a 1:1 mixture of water/brine. The extracted material was dried over sodium sulfate, concentrated and dried in vacuo.

The crude material, which was shown by TLC to be a complex mixture, was chromatographed on a Prep 500 eluting with ethyl acetate/hexane (3:1). The desired end product was isolated by concentrating the appropriate fractions and crystallizing the residue from ethyl acetate/hexane to give the tricyclic β-sulfoxide of the title as a crystalline substance.

EXAMPLE 8

(2R-(2α,4α,6β,7α)-4-methyl-8-oxo-7-[(phenylacetyl)-amino]-5-thia-1-azatricyclo[4.2.0.0$^{2,4}$]octane-2-carboxylic acid (4-nitrophenyl)methyl ester 0.803 g of the tricyclic β-sulfoxide of Example 7 was taken up in 20 mL of dry DMF and the solution cooled on an ice-acetone bath. Phosphorus tribromide (0.56 mL) was added dropwise. The mixture was stirred for 20 minutes at a temperature <0° C. The reaction mixture was poured into cold aqueous sodium bicarbonate (3.80 g in 190 mL of water). The mixture was extracted twice with 85 mL of ethyl acetate. The two organic extracts were combined and washed with 50 mL of 1° sodium bicarbonate, followed by water and finally brine. The organic phase was dried over Na$_2$SO$_4$ and concentrated.

The concentrated residue was taken up in ethyl acetate and filtered through a bed of silica in a scintered glass funnel eluting with ethyl acetate/hexane (1:1). Two fractions of approximately 200 mL each were collected and washed with ethyl acetate. Fraction 1 was concentrated and crystallized from ethyl acetate/hexane. The solid was collected and dried yielding the title compound, which was identical to the material isolated in Example 5.

EXAMPLE 9 p-Nitrobenzyl 5R-6β-Amino-2-methyl-(2,3)-α-methylene-penam-3-carboxylate

To a solution of p-nitrobenzyl 6-β-phenylacetylamino[2,3]-α-methylenepenicillinate, the product from example 3, (94 mg, 0.2 mmol) and pyridine (dry, 32 mL, 0.38 mmol) in dry CHCl$_3$ (2 mL) was added PCl$_5$ (46 mg, 0.22 mmol) at −4° to −2° C. The mixture was stirred at this temperature for 1 h. About 30 min after the addition of PCl$_5$, a white precipitate was formed. n-Propanol dried over molecular sieve (4 A) (0.3 mL) and then CHCl$_3$ (1 mL) were added at −4° to 2° C. After the reaction was stirred for about 45 min at same temperature, it became a clear solution. When precipitate still remained after 45 min., PCl$_5$ (2 mg) was added and stirred for 15 min until the reaction becomes clear. The addition was repeated if the precipitate did not dissolve. Usually, 2–4 mg PCl$_5$ were required. The reaction was further stirred for an additional 15 min after the clear solution was obtained. Subsequently, brine (0.5 mL) was added at 0° C. and the reaction stirred for 15 min. EtOAc (6 mL), brine (3 mL) and sat. NaHCO$_3$ (0.5 mL) were then added successively. The two layers were separated, and the organic phase was washed with brine (2×3 mL), dried over Na$_2$SO$_4$ and filtered. The filtrate was used as is for subsequent acylation rections. This material has Rf 0.35 with the system SiO$_2$/EtOAc.

EXAMPLE 10 p-Nitrobenzyl 5R-6β-Benzyloxcarbonylamino-2-methyl-(2,3)-α-methylene-penam-3-carboxylate The product from Example 9 in ethyl acetate (4 mL) prepared from 0.1 mm of p-nitrobenzyl 6-β-phenylacetylamino-[2,3]-α-methylene penicillinate, was treated at 0° C. with benzylchloroformate (22 {1, 0.15 mmol) in the presence of saturated NaHCO$_3$ (0.25 ml). The reaction was stirred at 0° C. for 1 h. The organic phase was separated, washed with brine (2×1 ml) and dried (Na$_2$SO$_4$). The filtrate was concentrated to about 1 ml and immediately purified on flash column chromatography eluted with ethyl acetate-hexane (1:2) to give the title compound (R$_f$0.37, EtOAc:Hexane=1:1). This compound was further purified by crystallization from EtOAc-Hexane.

EXAMPLE 11

[3R-[1(R*),3α,4α]]-4-(benzthiazol-2-yldithio)-α-(1-methylethenyl)-2-oxo-3-[[phenylacetyl)amino]-α-(1-methylethenyl)-2-oxo-3-[[(phenylacetyl)amino]-1-azetidineacetic acid (4-nitrophenyl)methyl ester.

[2S-(2α,4β,5α,6β]-3-dimethyl-7-oxo-6-[(phenylacetyl)amino-4-thia-1-azabicyclo-[3.2.0]-heptane-2-carboxylic acid (4-nitrophenyl)-methyl ester S-oxide (224 g, 0.46 mol) and 2-mercaptobenzothiazole (77 g, 0.46 mol) were combined and dissolved in 2300 mL of toluene in a 3-L round bottom flask fitted with a Dean-Stark apparatus. The clear, yellow solution was heated at reflux in an oil bath for 4 hours. The reaction produced 8 mL of water. The reaction mixture was concentrated in vacuo to an amber, viscous oil which was then diluted with 400 mL of warm chloroform followed by 500 mL of ether. Cooling to room temperature and refrigeration overnight provided crude end product which was triturated with 3 L of ether/chloroform (1:5:1, v/v) to provide crystalline product, homogeneous by TLC, EtOAc-hex (3:1 v/v).

EXAMPLE 12

[3R-[1(R*),3α,4α[[-4-(benzothiazol-2-yldithio)-3-](trifluoroacetyl)(phenylacetyl)amino]-α-(1-methylethenyl)-2-oxo-1-azetidineacetic acid (4-nitrophenyl)-methyl ester The disulfide of Example 11 (15.0 g, 23.6 mmole) was placed in a dry two-liter flask. Chloroform (115 ml, dried by passing through basic alumina) was added and the resultant mixture was stirred under argon for 5 minutes. Trifluoroacetic anhydride (100 g, 476 mmole) was added at once, and the resultant mixture was stirred at room temperature, under argon for 5 hours. The reaction mixture was concentrated at 35° C. and dried in vacuo (utilizing dry toluene to drive off the trifluoroacetic acid) yielding the crude imide.

EXAMPLE 13

2S-(2α,3α,5α,6β)[3-(bromomethyl)-3-methyl-7-oxo-6-[(phenylacetyl)amino]-4-thia-1-azabicyclo[3.2.0]heptane-2-carboxylic acid (4-nitrophenyl)methyl ester The crude imide of Example 12 (18.2 g, 23.6 mmole) was dissolved in methylene chloride (100 mL, dried over basic alumina), under argon. The reaction solution was cooled to −10° C. and calcium oxide (2.65 g, 47.3 mmole) was added. Bromine (56 mL of 0.195M solution in methylene chloride, 10.9 mmole) was added dropwise over 15 minutes and the resultant mixture was stirred for 10 minutes (bath temperature between −5° C. and −10° C.). A mixture of cold diethyl ether (290 mL) and petroleum ether (250 mL) was added and the resultant mixture was stirred for 10 minutes. The mixture was filtered through a bed of celite and the filtrate was concentrated and dried in vacuo to a foam. The foam was dissolved in cold acetone (275 mL/water (75 mL) and saturated sodium bicarbonate solution (16 mL) was added over a 5 minute period to bring the pH of the solution to between 7.3–7.5. Ethyl acetate (600 mL) was added and the resultant layers were separated. The organic layer was washed two times with saturated sodium chloride solution, dried over sodium sulfate, and concentrated, yielding crude material as a mixture of 3α- and 3β-bromomethyl penams. The crude material was chromatographed by High Pressure Liquid Chromatography using the Waters prep 500 instrument. Two columns were used for the separation. The material was eluted with ethyl acetate-hexane (2:3) at a flow rate of 250 mL/min. yielding the bromide. There was no clean separation of the 3α- and 3β-bromomethyl compounds. The 3β-bromomethyl was slightly less polar. The first fraction containing bromomethyl penams was, therefore, kept separate as it was enhanced in the 3β-bromomethyl compound.

EXAMPLE 14

[2R-(2α,4α,6β,7α]-4-methyl-8-oxo-7-[phenylacetyl)amino]-5-thia-1-azatricyclo[4.2.0.0$^{2,4}$]octane-2-carboxylic acid (4-nitrophenyl)methyl ester The bromide mixture of Example 13 i.e. Fractions 2–5 (8.55 g, 15.6 mmole) was dissolved in N,N-dimethylformamide (150 mL, dried over 4 A molecular sieves) and the resulting solution was cooled to −35° C. 1,5-Diazabicyclo[5.4.0]undec-5-ene in 90 mL N,N-dimethylformamide (dried over 4 A molecular sieves) was added dropwise over 20 minutes and the resulting solution was stirred for 15 minutes. The reaction mixture was poured into ice-cold 0.1N hydrochloric acid (250 mL), extracted with ethyl acetate (400 mL), and the resultant two layers were separated. The organic layer was extracted with ice-cold 0.1N hydrochloric acid (250 mL) and then two times with 1:1 water-saturated sodium chloride solution. The organic layer was dried over sodium sulfate, concentrated and dried in vacuo. The crude tricyclic compound was chromatographed by the Stille Flash method, eluting with chloroform (15)-ethyl acetate (1). The desired fractions were combined (Under these reaction conditions the 3β-bromomethyl compound remains to a large extent unreacted. It co-elutes with the α-cyclopropyl compound. On crystallization, pure α-cyclopropyl is obtained, which was identical to the material obtained from Example 5.

EXAMPLE 15

2R-(2α,4α,6β,7α)]-4-methyl-8-oxo-7-[(phenylacetyl)amino]-5-thia-1-azatricyclo[4.2.0.0./2,4/]octane-2-carboxylic acid sodium salt The cyclopropyl compound of Example 14 (60 mg, 0.13 mmol) was added to a mixture of 10% Pd/C (63 mg), ethyl acetate (6 mL), and 0.05M aqueous sodium bicarbonate (2.6 mLs 0.13 mmol NaHCO$_3$). The mixture was hydrogenated at atmospheric pressure and room temperature with vigorous magnetic stirring for 2 hours. Hydrogen uptake totaled 5.5 mL (47% of theoretical). The reaction mixture was filtered through prewashed Celite. Some catalyst seeped through. The phases were separated and the ethyl acetate layer was washed with water (5 mL). The aqueous wash was added to the aqueous reaction phase and was concentrated in vacuo to a volume of ca 0.5 mL. The concentrate was loaded onto a C-18 SEP-PAK cartridge (Waters Assoc.) and eluted with water (24 fractions, 0.5 mL each). Fractions 20 to 24 contained pure end product (TLC silica, EtOAc—AcOH—H$_2$O, 85:9:6, v/v/v, R$_f$ 0.62, after freeze-drying).

Fractions 10 to 19 contained a mixture of two products (TLC silica, EtOAc—AcOH—H$_2$O, 85:9:6, v/v/v, R$_f$ 0.62 (major), R$_f$ 0.50 (minor), after freeze drying). The mixture was chromatographed on a Whatman M9—ODS 2 column (reversed phase) on a Waters analytical HPLC (Solvent Program No. 6, 15 minute run, 4 mL/min flow rate, 100% CH$_3$OH). The major component was collected, concentrated in vacuo to remove methanol and was freeze-dried to give the end product.

EXAMPLE 16 p-Nitrobenzyl 5R-2-Methyl-6β-(2-thienyl)acetylamino-(2,3)-β-methylenepenam-3-carboxylate A solution of [2R-(2α,4α,6β,7α)]-4-methyl-8-oxo-7-amino-5-thia-1-azabicyclo-[4.2.0.0$^{2,4}$]octane-2-carboxylic acid (4-nitrophenyl)methyl ester prepared from 94.0 mg (0.200 mmol) of the phenylacetylamide (see Example 9) was stirred at 0° C. while 50 mg (0.180 mmol) of S-(2-thienyl-acetyl) mercaptobenzoxazole was added in one portion. After stirring for 1 hour, 2 mL of saturated aqueous NaHCO$_3$ was added and stirring continued at 0° C. for an additional 1 hour. The organic layer was separated, dried over anhydrous MgSO$_4$, and the solution concentrated to a volume of 2 mL. Flash chromatography (silica gel, 10:3:9; methylene chloride/ethyl acetate/hexane) afforded the desired acylated tricyclic compound.

EXAMPLE 17

5R-2-Methyl-6β-(2-thienyl)acetylamino-(2,3)-α-methylenepenam-3-carboxylic acid potassium salt A solution of the product of Example 16 (27 mg, 0.057 mmol) in 10 mL of methanol-tetrahydrofuran (1:1) was hydrogenated at atmospheric pressure with 30 mg of 10% palladium on carbon. After 2 h the catalyst was removed by filtration through celite and replaced with 30 mg of fresh catalyst. Hydrogenation was continued for 2 hours and the mixture again filtered through celite and the solvent removed in vacuo. The residue was dissolved in ethyl acetate (5 mL), water (2 mL) and potassium carbonate (570 {L of a 0.1M solution, 0.057 mmol) were added, and the mixture stirred for 15 minutes. The aqueous phase was separated and the organic phase washed with 1 mL of water. The aqueous portions were combined and purified by reverse phase chromatography (Whatman M9—Partisil 10-ODS-2, linear gradient, 0–100%, methanol in water) to afford the end product as an off-white lyopholized powder.

EXAMPLE 18 p-Nitrobenzyl 5R-6-β-[Z-(2-amino-4-thiazolyl)-Z-(methoxyimino)-acetyl]amino-2-methyl-(2,3)-α-methylenepenam-3-carboxylate A solution of [2R-(2α,4α,6β,7α)]-4-methyl-8-oxo-7-amino-5-thia-1-azabicyclo-[4.2.0.0$^{2,4}$]octane-2-carboxylic acid (4-nitrophenyl)methyl ester in ethyl acetate (8 mL) prepared from the phenylacetyl compound (0.2 mmol) was treated with S-(2-benzothiazolyl)-2-amino-4-thiazoleglyoxylate (E)-O-methyloxime (60 mg, 0.18 mmol) at room temperature. The reaction mixture was concentrated to about 3 mL in vacuo and stirred at room temperature for 1.5 hour. After the reaction was completed (determined by TLC, SiO$_2$/EtOAc), the mixture was washed with aq. NaHCO₃, brine and dried (Na₂SO₄). Purification using flash column chromatography, EtoAc-Hexane=3:1, gave the end product: $R_f$ 0.33, SiO₂/EtOAc.

EXAMPLE 19

5R-6-β-[2-(2-Amino-4-thiazolyl)-Z-(methoxyimino)acetyl]amino-2-methyl-(2,3)-α-methylenepenam-3-carboxylic acid sodium salt The mixture of the end product of Example 18 (33 mg, 0.06 mmol), 10% Pd/c (40 mg) and 0.1M NaHCO₃ solution (0.7 ml) in ethylacetate (2 ml)—water (3 mL) was hydrogenated at atmospheric pressure, room temperature for 1.5 hour. The aqueous layer was separated and concentrated in vacuo at 10° C. to about 1 mL. Purification on C₁₃ Seppak, eluting with water, gave after freezed-drying the end product $R_f$ 0.25, SiO₂-/EtOAc:HOAc:H₂O (60:3:1).

EXAMPLE 20

P-Nitrobenzyl-5R-6-β-[(2-amino-4-thiazolyl)-Z-(1-methyl(1-p-nitrobenzyloxycarbonylethoxyimino)acetyl]amino-2-methyl-(2-methyl-(2,3)-α-methylenepenam-3-carboxylate To the methylene chloride solution of [2R-(2α,-4α,6β,7α]-4-methyl-8-oxo-7-amino-5-thia-1-azabicyclo-[4.2.0.0²,⁴]octane-2-carboxylic acid (4-nitrophenyl)-methyl ester [prepared from phenylacetyl derivative (140 mg, 0.3 mmol)] was added p-nitrobenzyl-2-[[[[2-amino-4-thiazolyl]-[(2-benzothiazolylthio)carbonyl]methylene]amino]oxy]-2-methyl propionate (143.2 mg 0.257 mmol). The resulting solution was stirred at room temperature for 3 hours under an atmosphere of argon. The reaction mixture was washed once with saturated sodium bicarbonate solution, once with saturated sodium chloride solution. The organic layer was dried over anhydrous sodium sulfate, then filtered. The filtrate was concentrated in vacuo at 10 mmHg, 15° C. to a small volume which was then purified by flash chromatography (silica gel 400-63 {; eluted with ethyl acetate-hexane 7:3) to afford the end product; NMR suggests desired product and tri-n-propyl phosphate present).

EXAMPLE 21

5R-6-β-[(2-Amino-4-thiazolyl)-Z-(1-methyl-1-carboxyethoxyimino)-acetyl]amino-2-methyl-(2,3)-α-methylenepenam-3-carboxylic acid disodium salt A solution of the end product of Example 20 (79.7 mg, 0.108 mmole) in N,N-Dimethylformamide (5.0 mL, dried over molecular sieves 4 A) was hydrogenolyzed for 2 hours at room temperature, one atmospheric pressure in presence of a suspension of 10% Pd/C (80.0 mg). The solution was filtered through celite. The filtrate was concentrated in vacuo at 1 mmHg, 23° C. to a gum, which was dissolved in a small volume of methanol in presence of an aqueous solution of sodium bicarbonate (18.1 mg, 0.215 mmol). The homogeneous mixture was stirred for a few minutes, then deionized water was added. This was washed twice with ethyl acetate. The organic wash was back washed once with deionized water. The aqueous extracts were combined (PH 7.0) and concentrated in vacuo at 1 mmHg, 20° C. to a small volume which was purified by column chromatography (HP-20 resin, water) to afford the end product as a pale yellow solid.

EXAMPLE 22

[2R-[2α,4α,6β,7α(R*)]]-7-[(α-hydroxyphenylacetyl)amino]-4-methyl-8-oxo-5-thia-1-azatricyclo-[4.2.9.9./2,4/]-octane-2-carboxylic acid (4-nitrophenyl)-methyl ester D-Mandelic acid (14 mg, 0.092 mmol), dicyclohexylcarbodiimide (19 mg, 0.092 mmol) and 1-hydroxybenzotriazole (13 mg, 0.096 mmol) were combined and dissolved in a mixture of 2 mL of chloroform (dried over 4 A sieves). The solution was stirred under argon while cooled in a brine-ice bath (−2° to 0° C.) for 40 minutes. An ethyl acetate solution of [2R-(2α,4α,6β,7α)[-4-methyl-8-oxo-7-amino-5-thia-1-azabicyclo-[4.2.0.0²,⁴]octane-2-carboxylic acid (4-nitrophenyl)methyl ester prepared from 0.1 mmol of phenylacetyl derivative was added and the mixture concentrated in vacuo to a volume of ca 3 mL. After 3.5 hours at −2° to 0° C., the reaction mixture was diluted with ethyl acetate, transferred to a separatory funnel and washed with brine (2×5 mL) and saturated aqueous sodium bicarbonate (2×5 mL). The ethyl acetate layer was separated, dried (MgSO₄) and concentrated in vacuo, chromatography on silica (plate, 20×20 mm, 0.25 mm thickness, ethyl acetate/methylene chloride, 1:4 v/v) provided the end product. The end product was crystallized from a mixture of ethyl acetate/methylene chloride/hexanes: mp 183°–187° C.

EXAMPLE 23

[2R-[2alpha,4alpha,6beta,7alpha(R*)]]-7-[(Phenylhydroxyacetyl)amino]-4-methyl-8-oxo-5-thia-1-azatricyclo[4.2.9.9./2,4/]-octane-2-carboxylic acid, sodium salt 10% Pd/C (46 mg) was combined with ethyl acetate (9 mL), sodium bicarbonate (8 mg, 0.095 mmol) and water (2 mL) in a 25 mL round bottomed flask containing a magnetic stir bar. The contents were stirred under an atmosphere of hydrogen at atmospheric pressure and room temperature (22> C.) until hydrogen uptake ceased (ca. 30 minutes). The the product from Exmaple 22 (46 mg, 0.095 mmol) was added and the heterogeneous mixture was stirred vigorously under hydrogen for two hours. A total of 5 mL of hydrogen was taken up. The reaction mixture was filtered through celite (pre-washed with water). The filter-cake was rinsed with water and the rinsing was combined with the filtrate. The aqueous phase was separated and concentrated in vacuo to ca. 1 mL. This concentrate was passed through a Swinnex GS (0.22 um) filter and two C-18 SEP-PAKS in series. Elution with water gave after freeze-drying the end product.

EXAMPLE 24

P-Nitrobenzyl 5R-6β-(D-2-Benzyloxycarbonylaminophenylacetyl)amino-2-Methyl-(2,3)-α-methylenepenam-3-carboxylate To the solution of D-2-benzyloxycarbonylaminophenyl acetic acid (85.5 mg, 0.3 mmol) and N-hydroxybenzotriazole (42 mg, 0.3 mmol) in dry CHCl₃ (3 mL) and DMF (0.1 mL) was added N,N'-dicyclohexylcarbodiimide (66 mg, 0.33 mmol) and the mixture were stirred at room temperature for 1 hour. The solution of [2R-(2α,-4α,6β,7α]-4-methyl-8-oxo-7-amino-5-thia-1-azabicyclo-[4.2.0.0²,⁴]octane-2-carboxylic acid (4-nitrophenyl)-methyl ester in CHCl₃ (8 mL) prepared from phenylacetyl derivative (141 mg, 0.3 mmol) was then added and the total volume of the reaction was reduced to about 3 mL in vacuo. After stirring at 0° C. for 1.5 hour, aqueous NaHCO₃ (1.5 mL) was added and stirred at same temperature for 30 minutes. The reaction mixture was dissolved in CHCl₃ (10 mL), and washed with water (3 mL). The organic phase was dried (Na₂SO₄) and concentrated to 2 mL. Ether (3 mL) was then added and the mixture was filtered to remove the urea by-product. The mother liquor was evaporated to about 1.5 mL and purified on flash column chromatography (80 g silica gel) eluted with 10% EtOAc-CHCl₃ to give the end product: R$_f$0.35 (10% EtOAc-CHCl₃).

EXAMPLE 25

2R-(2β,4β,6α,7α)]-7-Methoxy-4-methyl-8-oxo-7-[(phenylacetyl)amino]-5-thia-1-azatricyclo[4.2.0.0/2,4/]octane-2-carboxylic acid (4-nitrophenyl)methyl ester To a stirred solution of the cyclopropyl compound of Example 3 (93.0 mg, 0.2 mmol) in anhydrous dichloromethane (1 mL) at −30° C. under an argon atmosphere, was simultaneously added tert. butyl hypochlorite (32.3 mg, 0.27 mmol) and a methanolic lithium methoxide solution (170 μL containing 8 mg of LiOMe, 0.2 mmol). After stirring at −30° C. for 30 minutes the mixture was purified by HPLC (Whatman MO Partisil 10, linear gradient 25°–70° solvent mixture B in solvent mixture A; A=isooctane/dichloromethane 1:2; B=ethyl acetate/dichloromethane 1:2) to afford recovered starting β-lactam, a mixture of β-lactam ring opened methyl esters of product and starting material, and the desired methoxylated product as a pale yellow, tacky solid.

EXAMPLE 26

[2R-(2β,4β,6α,7α)]-7-Methoxy-4-methyl-8-oxo-7-[(phenylacetyl)amino]-5-thia-1-azatricyclo[4.2.0.0/2,4/]-octane-2-carboxylic acid sodium salt A solution of the p-nitrobenzylester of Example 24 (25 mg, 0.05 mmol) in anhydrous tetrahydrofuran-methanol (1:1, 5 mL) was hydrogenated over 10% palladium on carbon (28 mg) at atmospheric pressure. After 2 hours the catalyst was removed by filtration through celite and the celite washed with methanol (3×2 mL). To the combined filtrate and washings was added an aqueous solution of sodium bicarbonate (8 mL), containing 4.4 mg, 0.05 mmol of NaHCO₃) and the volume reduced to 5 mL (vacuum, ambient temperature). The resulting solution was extracted with dichloromethane (1×3 mL) and the aqueous layer was then purified by reverse phase liquid chromatography (Whatman M9-Partisil 10-ODS-2, linear gradient 0–100% methanol/water) to afford the end product as a white lyophilized powder: mp 159°–161° C.

EXAMPLE 27

[2R-[2β,4β,6α,7β(R,S)]]-α-[[[4-Methyl-2-[[(4-nitrophenyl)methoxy]carbonyl]-8-oxo-5-thia-1-azatricyclo[4.2.0.0²,⁴]-oct-7-yl]amino]carbonyl]benzene acetic acid (4-nitrophenyl)methyl ester

[2R-(2α,4α,6β,7α)]-4-methyl-8-oxo-7-[(phenylacetyl)amino]-5-thia-1-azatricyclo[4.2.0.0²,⁴]-octane-2-carboxylic acid (4-nitrophenyl) methyl ester (126 mg, 0.269 mmoles) was prepared following the experimental procedure of Example 9.

Thereafter phenylmalonic acid mono-p-nitrobenzyl ester (0.85 mg, 0.269 mmol) was dissolved in thionyl chloride (0.25 mL, 3.49 mmol). The solution was heated at 70° C. for one hour. After cooling to room temperature, the solution was concentrated in vacuo and toluene was co-evaporated from the residue in vacuo. The crude acid chloride was then dissolved in dry chloroform (2 mL) and added at 0° C. to the basified deacylation mixture prepared following Example 9. This mixture was stirred under argon atmosphere at −5° C. to 0° C. for two hours. The phases were separated and the aqueous phase extracted with ethyl acetate (2×10 mL). The ethyl acetate extracts were combined with the organic phase which was subsequently washed with saturated sodium chloride solution (2×10 mL). The organic layer was dried over sodium sulfate, filtered, concentrated in vacuo and chromatographed on silica gel (35 g, column; ethyl acetate/hexane/methylene chloride, 1:2:3, (v/v/v) as eluent) to give the end product as a viscous oil after drying in vacuo.

EXAMPLE 28

[2R-[2β,4β,6α,7β(R,S)]]-α-[[[2-(carboxy)-4-methyl-8-oxo-5-thia-1-azatricyclo[4.2.0.0²,⁴]oct-7-yl]amino]carbonyl]benzeneacetic acid disodium salt A solution of the end product of Example 27 (42 mg 0.065 mmol) in distilled tetrahydrofuran (3 mL) was added to pre-hydrogenated catalyst (10% Pd/C, 42 mg) in dry THF (2 mL). The mixture was stirred under hydrogen atmosphere for three hours. The mixture was filtered through pre-washed Celite and the filter cake was rinsed with THF. The filtrate and rinsings were combined and treated with water (2 mL) containing sodium bicarbonate (0.13 mmol). After vigorous mixing, the aqueous phase was washed with ether (2×10 mL) and concentrated in vacuo. The concentrate was chromatographed on a reverse phase C-18 column (10 g, flash, water as eluent) to give the end product as a white powder after freeze-drying.

EXAMPLE 29

[2R-(2β,4β,6α,7β)]-7-[(cyanoacetyl)amino]-4-methyl-8-oxo-5-thia-1-azatricyclo[4.2.0.0.²,⁴]octane-2-carboxylic acid Dicyclohexylcarbodiimide (102 mg, 0.49 mmol) was added in one portion to the suspension of cyanoacetic acid (39 mg, 0.45 mmol) and 1-hydroxybenzotriazole hydrate (73.4 mg, 0.48 mmol) in dichloromethane (3 mL with magnetic stirring and cooling in an ice-water bath. After 90 min., a dried solution (MgSO₄) of [2R-(2α, 4α, 6β, 7α)]-4-methyl-8-oxo-7-[(phenylacetyl)amino]-5-thia-1-azatricyclo[4.2.0.0²,⁴]-octane-2-carboxylic acid (4-nitrophenyl) methyl ester, prepared from [2R-(2α, 4α, 6β, 7α)]-4-methyl-8-oxo-7-[(phenylacetyl)amino]-5-thia-1-azatricyclo[4.2.0.0²,⁴]-octane-2-carboxylic acid (4-nitrophenyl)methyl ester (208.2 mg, 0.44 mmol) by the procedure mentioned above using dichloromethane instead of ethyl acetate as solvent, was added to this suspension. The mixture was stirred with cooling in an ice-water bath for 2 h followed by stirring at room temperature for 1 h. Reaction mixture became a clear solution and was chromatographed on silica gel (flash chromatography, 150 g, ethyl acetate—dichloromethane, 1:4, v/v, as solvent, collecting 100 mL per flask). Flasks 6 to 10 were combined and concentrated to give crude [2R-(2β, 4β, 6α, 7β)-7-[(cyanoacetyl)amino]-4-methyl-8-oxo-5-thia-1-azatricyclo[4.2.0.0.²,⁴]octane-2-carboxylic acid (4-nitrophenyl) methyl ester which was used in the next step without further purification.

The crude intermediate (71.6 mg, 0.17 mmol) was dissolved in dry tetrahydrofuran (10 mL) and mixed with 10% palladium on carbon (80 mg). This mixture was hydrogenated at atmospheric pressure and room temperature until hydrogen uptake stopped (approximately 2 h). The reaction mixture was filtered through Celite (pre-washed with acetonitrite), and the filter-cake washed with acetonitrile (20 mL). Filtrate and washing were combined and added to the solution of sodium bicarbonate (14.4 mg, 0.17 mmol) in water (20 mL). This solution was concentrated under reduced pressure to remove organic solvents. The resulting aqueous solution was diluted with water to about 20 mL and extracted with an equal volume of dichloromethane. After separating the layers, the aqueous phase was again concentrated to a small volume under reduced pressure. The yellow precipitate formed was removed by filtration. This filtrate was diluted with water to 8 mL, and purified in three runs by reverse phase chromatography (Whatman Partisil M9, 10/25, ODS-2 column, 4 mL/min flow rate, water as solvent, using an injector with a 5 mL-injection loop). End product was eluted with a retention time of 9–5 min. After combining the fractions from the two runs, lyophilization gave a white solid.

EXAMPLE 30

[2R-(2β,4β,6α,7β)]-7-[[Hexahydro-1H-azepin-1-yl) methylene]amino]-4-methyl-8-oxo-5-thia-1-azatricyclo[4.2.0.0$^{2,4}$]octane-2-carboxylic acid monosodium salt To a solution (186.8 mg, 0.4 mmol) of crude [2R-(2α,4α,6β,7α)]-4-methyl-8-oxo-7-amino-5-thia-1-azatricyclo[4.2.0.0$^{2,4}$]octane-2-carboxylic acid (4-nitrophenyl)methyl ester (prepared following the experimental procedure of Example 9 from the 7-[(phenylacetyl)amino]analog in methylene chloride) was added a solution of p-toluenesulfonic acid monohydrate (57.0 mg, 0.3 mmol) and triethylamine (42 μl, 0.3 mmol) in methylene chloride (2.0 mL). To the resulting mixture was added the dimethyl acetal of N-formylhexamethyleneimine (89° pure; 520 mg, 2.67 mmol) at 0° C. The reaction mixture was stirred at 0° C. overnight under an atmosphere of argon. The solvent was removed in vacuo at 10° C. 110 mm Hg. The crude residue was extracted twice with ethyl acetate and backwashed three times with deionized water, once with a saturated solution of sodium bicarbonate, twice with deionized water. The ethyl acetate extracts were combined, dried over anhydrous sodium sulfate and filtered. The filtrate was concentrated to dryness in vacuo to afford the p-nitrobenzyl ester of the title compound as a crude dark oil.

The oil was dissolved in ethyl acetate (4.0 mL) in the presence of 10% Pd/C (150 mg). To this mixture was added a solution of sodium bicarbonate. (34.0 mg, 0.4 mmol) in deionized water (4.0 mL). The resulting mixture was stirred under hydrogen (1 atm) for 2 hours at ambient temperature. The mixture was filtered through Celite, washed with water and ethyl acetate. The aqueous portion was separated from the ethyl acetate. The organic portion was washed once with deionized water. Aqueous extracts were combined and concentrated in vacuo at 20° C. to a second volume which was then purified by column chromatography (HP-20 resin; 10–20% CH$_3$CN/water) to afford crude end product as a pale yellow solid. This was further purified by high pressure chromatrography (Whatman Partisil M9 10/25 OD5-2; Ch$_3$CN/water) to afford pure end product as a colorless solid.

EXAMPLE 31

[2R-(2β,4β,6α,7β)]-4-Methyl-8-oxo-7[(phenoxyacetyl)amino]-5-thia-1-azatricyclo[4.2.0.0$^{2,4}$]octane-2-carboxylic acid sodium salt To a solution of crude [2R-(2α,4α,6β,7α)]-7-amino-4-methyl-8-oxo-5-thia-1-azatricyclo[4.2.0.0$^{2,4}$]octane-2-carboxylic acid (4-nitrophenyl)methyl ester as prepared in Example 9 (140.1 mg; 0.3 mmol) in methylene chloride was added a solution of potassium bicarbonate (75.0 mg, 0.75 mmol) in deionized water (5.0 mL). To the resulting mixture was added phenoxyacetyl chloride (20.7 {1, 0.15 mmol) at 0° C. The reaction mixture was stirred at 0° C. for 2 hrs. The reaction was monitored by TLC. The mixture was then brought to room temperature and was stirred for another 30 minutes. A saturated solution of sodium bicarbonate was added and stirred for a few minutes. The organic layer was separated from the aqueous portion. The aqueous portion was extracted once more with methylene chloride, and the organic extracts were washed once with brine and then combined and dried over anhydrous sodium sulfate. The mixture was filtered, and the filtrate was concentrated in vacuo at 10° C./10 mm Hg to near dryness. The crude material was purified by flash chromatography (silica gel, 40–63 {, CH$_2$Cl$_2$- EtOAC-Hexane (70/10/20) to afford the title compound as its p-nitrobenzyl ester.

The ester (29.2 mg; 0.0603 mmol) was hydrogenated in THF (5.0 mL) at ambient temperature, one atmospheric pressure in presence of 10% Pd/C (60.0 mg) for 1½ hr. The mixture was filtered through Celite. To the filtrate was added a solution of sodium bicarbonate (5.06 mg, 0.0603 mmol) in deionized water. The mixture was stirred and the organic solvent was removed in vacuo at 20° C./10 mm Hg. The aqueous portion was extracted twice with ethyl acetate. The organic extracts were backwashed once with deionized water. The aqueous portions were combined and concentrated in vacuo at 20° C./1 mm Hg to a small volume which was then purified by column chromatography (HP-20 resin, 10–20% CH$_3$CN/water) to afford end product as a pale yellow solid. This was further purified by high pressure liquid chromatography (Whatman Partisil M9 10/25 ODS-2; CH$_3$CN/ water) to afford pure end product.

EXAMPLE 32

2R-2-[[(4-Ethyl-2,3-dioxo-1-piperazinyl)carbonyl]amino]phenylthiolacetic acid-S-(benzothiazol-2-yl) ester To a stirred solution of 2-mercaptobenzothiazole (42 mg, 0.25 mmol) and D-2-[[(4-ethyl-2,3-dioxo-1-piperazinyl) carbonyl]amino]phenylacetic acid (80 mg, 0.25 mmol) in anhydrous dichloromethane (4 mL) at ambient temperature was added a solution of dicyclohexylcarbodiimide (52 mg, 0.25 mmol) in dichloromethane (1 mL). The resulting mixture was stirred at room temperature for 3 h, filtered to remove the dicyclohexylurea, and the filtrate used directly in the coupling step.

EXAMPLE 33

[2R-[2β,4β,6α,7β,(R*)]]-7-[[[[(4-ethyl-2,3-dioxo-1-piperazinyl)carbonyl]amino]phenylacetyl]amino]-4-methyl-8-oxo-5-thia-1-azatricyclo[4.2.0.0$^{2,4}$]octane-2-carboxylic acid (4-nitrophenyl)methyl ester To the dichloromethane solution of the benzotriazolyl thio acid was added at room temperature a dried (Na$_2$SO$_4$) chloroform solution (7 mL) of p-nitrobenzyl-6β-amino-(2,3)-α-methylenepenicillanate [prepared from p-nitrobenzyl-6β-(phenylacetyl)amino-(2,3)-α-methylenepenicillanate (117 mg, 0.25 mmol), phosphorus pentachloride (57.5 mg, 0.27 mmol), pyridine (25 {L, 0.31 mmol) and n-propanol (185 {L, 2.5 mmol)

essentially as described previously (vide supra)]. The resulting solution was stirred at ambient temperature for 2 h and then partially purified by flash chromatography (silica, ethyl acetate as eluent). Further purification was effected by HPLC (Whatman M-9 Partisil 10–25, linear gradient over 20 min, 0–50% solvent mixture B in solvent mixture A; A=dichloromethane/ethyl acetate 2:1, B=dichloromethane/ethyl acetate 1:1). The major component was rechromatographed on the same column (linear gradient over 20 min, 25–35% solvent mixture C in solvent mixture D, C=chloroform/isopropanol 95:5; D=chloroform/isooctane 80:20). This afforded two relatively pure fractions. The first fraction does not contain the β-lactam ring [IR,NMR, on isolated solid] whereas the second fraction on removal of solvent afforded the desired acylated β-lactam as a white powdery solid.

EXAMPLE 34

[2R-[2β,4β,6α,7β(R*)]]-7-[[[[(4-ethyl-2,3-dioxo-1-piperazinyl)carbonyl]amino]phenylacetyl]amino]-4-methyl-8-oxo-5-thia-1-azatricyclo[4.2.0.0./2,4/]octane-2-carboxylic acid monosodium salt A solution of the p-nitrobenzyl ester from Example 33 (25 mg, 0.038 mmol) in anhydrous tetrahydrofuran (1 mL) was added to a suspension of prehydrogenated 10% palladium on carbon in anhydrous tetrahydrofuran (3 mL) and the resulting mixture stirred under hydrogen at atmospheric pressure. After 2 h, the catalyst was removed by filtration through Celite an the Celite and catalyst washed with tetrahydrofuran (2×3 mL). To the combined filtrate and washings was added an aqueous solution of sodium bicarbonate (8 mL, containing 3.5 mg, 0.04 mmol of $NaHCO_3$) and the volume reduced to 5 mL (vacuum, ambient temperature). The resulting solution was extracted with dichloromethane (2×3 mL) and the aqueous layer was purified by reverse phase liquid chromatography (Whatman M9-Partisil 10-ODS-2, linear gradient 0–40% acetonitrile in water) to afford the piperacillin tricyclic compound of the title as a white lyophilized powder.

EXAMPLE 35

[2R-[2α,4α,6β,7α(R*)]]-4-methyl-8-oxo-7-[[[[(2-oxo-1-imidazolidinyl)carbonyl]amino]phenylacetyl]amino]-5-thia-1-azatricyclo[4.2.0.0$^{2,4}$]octane-2-carboxylic acid (4-nitrophenyl) methyl ester Dicyclohexylcarbodiimide (86.7 mg, 0.42 mmol) added in one portion to the solution of [[(2-oxo-1-imidazolidinyl) carbonyl]amino]phenylacetic acid (96.9 mg, 0.37 mmol) and 2-mercaptobenzothiazole (67.0 mg, 0.40 mmol) in ethyl acetate (3 mL) with magnetic stirring at room temperature. A white precipitate formed. After 1 h, a dried solution ($MgSO_4$) of p-nitrobenzyl-6β-amino-(2,3)-α-methylenepenicillinate, prepared as described in Example 9 from p-nitrobenzyl-6β-(phenylacetyl)amino-(2,3)-α-methylenepenicillinate (198.6 mg, 0.42 mmol) was added to this suspension. This mixture was stirred at room temperature for an additional 2 h. Insoluble material was filtered off, and the filtrate was chromatographed on silica gel (flash chromatography 120 g silica gel, ethyl acetate as solvent, collecting 100 mL per Fraction). Fractions 5 to 11 were combined and concentrated. The residue was rechromatographed by preparative thin-layer chromatography (ten 20×cm plates, 0.25 mm thickness, E. Merck. silica gel 60 F-254) using 2-propanolchloroform (5:95 v/v as solvent and developing 4 times. The band with final Rf of 0.49 was collected. The end product was eluted off with ethyl acetate-2-propanol and concentrated to give pure end product.

EXAMPLE 36

[2R-[2α,4α,6β,7α,(R*)]]-4-methyl-8-oxo-7-[[[[2-oxo-1-imidazolidinyl)carbonyl]amino]phenylacetyl]-amino]-5-thia-1-azatricyclo[4.2.0.0$^{2,4}$]octane-2-carboxylic acid The end product of Example 35 (60 mg, 0.1 mmol) was dissolved in dry tetrahydrofuran (10 mL), and mixed with 20% palladium on carbon (60 mg). This mixture was stirred under one atmosphere of hydrogen at room temperature for 2 h. An additional portion of catalyst (60 mg) was added and hydrogenation was continued until the uptake of hydrogen stopped (another 45 min). The reaction mixture was filtered through Celite (prewashed with tetrahydrofuran), and the filter-cake washed with dry tetrahydrofuran (10 mL). The filtrate and washing were combined and added to a solution of sodium bicarbonate (10 mg, 0.12 mmol) in water (20 mL). This mixture was concentrated under reduced pressure to remove tetrahydrofuran. The resulting aqueous solution was extracted with an equal volume of dichloromethane. After separating the layers, the aqueous phase was further concentrated to a small volume under reduced pressure. A yellow precipitate was formed. This suspension (about 2 mL) was filtered and the filtrate was diluted with water to 4 mL and subjected to reverse phase chromatography (Whatman Partisil M9, 10/25 ODS-2 column, 4 mL/min, flow rate, 30 min, linear program of water to 40% acetonitrile in water, using an injector with a 5 mL-injection loop). The end product was eluted with a retention time of 16 min. After combining the appropriate fractions, lyophilization gave the end product as a white solid.

EXAMPLE 37

2R-[2β, 4β,6α,7β(R*)]]-7-[[(formyloxy)phenylacetyl]-amino]-4-methyl-8-oxo-5-thia-1-azatricyclo[4.2.0/2,4-/]octane-2-carboxylic acid (4-nitrophenyl)methyl ester (R)-α-(Formyloxy)-benzeneacetyl chloride was prepared by treating O-formyl-D-mandelic acid (58.2 mg, 0.323 mmoles) with excess thionyl chloride (37.7 μL, 0.517 mmoles) at 70° C. for 2 hours. After cooling to room temperature, the mixture was concentrated in vacuo. Toluene was added and evaporation in vacuo was repeated. The (R)-α-(formyloxy)benzeneacetyl chloride was then dissolved in dry chloroform (stored over 4 A seives, 2 mL) and added to p-nitrobenzyl 5R-6β-amino-2-methyl-(2,3)-α-methylene-penam-3-carboxylate (prepared from 150.4 mg, 0.323 mmoles of phenylacetyl derivative as previously described).

After stirring at −8 to −2° C. for 2 hours, the standard work-up procedure was performed followed by column chromatography on silica gel (30 g; ethyl acetate/hexane, 1:4 [v/v]) to give pure [2R-[2β,4β,6α,7β(R*)]]-7-[[(formyloxy)phenylacetyl-]amino]-4-methyl-8-oxo-5-thia-1-azatricyclo[4.2.0/2,4-/]octane-2-carboxylic acid (4-nitrophenyl)methyl ester (19.2 mg, 11%) and a mixture containing [2R-[2β,4β,6α,7β(R*)]]-7-[[(formyloxy)phenylacetyl-]amino]-4-methyl-8-oxo-5-thia-1-azatricyclo[4.2.0/2,4-/]octane-2-carboxylic acid (4-nitrophenyl)methyl ester. The mixture was chromatographed on thin-layer plates (silica gel, 20×20 cm, 2 mm thickness; ethyl acetate/hexane, 1:1 [v/v]) to provide additional [2R-[2β,4β,6α,7β(R*)]]-7-[[(formyloxy)phenylacetyl-]amino]-4-methyl-8-oxo-5-thia-1-azatricyclo[4.2.0/2,4-

/]octane-2-carboxylic acid (4-nitrophenyl)methyl ester (22.6 mg, 14%). The overall yield of [2R-[2β,4β,6α,7β(R*)]]-7-[[(formyloxy)phenylacetyl-]amino]-4-methyl-8-oxo-5-thia-1-azatricyclo[4.2.0.0/2,4-/]octane-2-carboxylic acid (4-nitrophenyl)methyl ester was 41.8 mg (25%).

EXAMPLE 37a

[2R-[2β,4β,6α,7β(R*)]]-7-[[(formyloxy)phenylacetyl-]amino]4-methyl-8-oxo-5-thia-1-azatricyclo[4.2.0.0/2,4-/]octane2-carboxylic acid monosodium salt Catalyst (10% Pd/C, 45 mg) was suspended in dry THF (2.0 mL, distilled over ketyl) and stirred under hydrogen atmosphere for 1 hour. A solution of 2R-[2β,4β,6α,7β(R*)]]-7-[[(formyloxy)phenylacetyl-]amino]-4-methyl-8-oxo-5-thia-1-azatricyclo[4.2.0.0/2,4-/]octane-2-carboxylic acid (4-nitrophenyl)methyl ester (45 mg, 0.088 mmole) in THF (4.0 mL) was added and the mixture stirred under hydrogen atmosphere at 21° C. for 3.5 hours. The reaction mixture was filtered through prewashed Celite and the filter cake rinsed with THF. The combined filtrate and rinsings were thoroughly mixed with sodium bicarbonate (7.4 mg, 0.088 mmole) in water (20 mL). The aqueous phase was washed with ethyl acetate (50 mL), concentrated in vacuo and chromatographed (Waters Analytical HPLC; Whatman-M9 ODS-2 reversed phase column; water/acetonitrile, linear gradient) to provide title compound (9.0 mg, 26%) as a freeze-dried, white powder.

EXAMPLE 38

[2R-(2α,4α,6β,7α)]-7-[[[(2,6-dichloro-4-pyridinyl)thio]acetyl]amino]-4-methyl-8-oxo-5-thia-1-azatricyclo [4.2.0.0/2,4/]octane-2-carboxylic acid (4-nitrophenyl)-methyl ester A solution containing 0.117 mmole of the amine p-nitrobenzyl 5R-6β-amino-2-methyl-(2,3)-α-methylene-penam-3-carboxylate, in dry chloroform was cooled in an ice/water bath, treated with 54 μL, 0.387 mmole, 3.3 equivalent triethylamine and a dropwise solution of 0.351 mmole of 2,6-dichloro-4-pyridyl)thio]acetyl chloride hydrochloride in 1.0 mL of dry CH$_2$Cl$_2$ was added dropwise. The reaction was stirred 1 hr. 15 min, stripped to dryness and stored overnight in the freezer.

All the material from above was dissolved in methylene chloride/ethyl acetate and chromatographed on silica gel to give the title compound.

EXAMPLE 39

[2R-(2alpha,4alpha,6beta,7alpha)]-7-[[[(2,6-Dichloro-4-pyridinyl)thio]acetyl]amino]-4-methyl-8-oxo-5-thia-1-azatricyclo[4.2.0.0/2,4/]octane-2-carboxylic acid sodium salt A solution of 31.8 mg, 0.055 mmole, of [2R-(2α,4α,6β,7α)]-7-[[[(2,6-dichloro-4-pyridinyl) thio]acetyl]amino]-4-methyl-8-oxo-5-thia-1-azatricyclo [4.2.0.0/2,4/]octane-2-carboxylic acid (4-nitrophenyl)-methyl ester in 4.0 mL of tetrahydrofuran/methanol (1:1) was treated with 26.1 mg of 10% Palladium on Carbon, and hydrogenated at one atmosphere for 1½ hours. The solution was filtered through Celite and the pad was washed with 20 mL of additional THF/MeOH (1:1). A solution of 6.6 mg, 0.078 mmole, 1.40 equivalents of Sodium bicarbonate in 2.0 mL of H$_2$O was added and the organic solvents were removed on a rotary evaporator. The aqueous solution was washed with 2×20 mL each of ethyl acetate and lyophilized to give 12.3 mg of yellowish powder.

All the above was dissolved in a small amount of H$_2$O and chromatographed on a C-18 reverse phase column using a 0% to 50% acetonitrile/H$_2$O gradient. The appropriate fractions were combined and lyophilized to give 3.4 mg, 13%, of the title compound.

EXAMPLE 40

[2R-(2beta,4beta,6alpha,7beta)]-7-[[(2,6-Dimethoxyphenyl) carbonyl]amino]-4-methyl-8-oxo-5-thia-1-azatricyclo [4.2.0.0/2,4/]octane-2-carboxylic acid (4-nitrophenyl)methyl ester A 0.1 mmol solution of p-nitrobenzyl 5R-6β-amino-2-methyl-(2,3)-α-methylene-penam-3-carboxylate in 1.0 mL of chloroform and 4.0 mL of ethyl acetate was cooled in an ice/water bath and treated with 2.0 mL of saturated Sodium bicarbonate. To this was added a total of 403.3 mg, 2.0 mmol, of 2,6-dimethoxybenzoylchloride in two portions at half-hour intervals. After stirring a total of one hour, the aqueous phase was separated and the organic phase was washed 4 times with 1.0 mL of saturated Sodium bicarbonate. The organic solution was dried with Magnesium sulfate, filtered and concentrated to dryness on a rotary evaporator to give 88.2 mg of crude material.

All of the above was dissolved in hexanes/ethyl acetate (1:2) and chromatographed on silica gel to give 69.3 mg of partially purified material. This was dissolved in ethyl acetate and chromatographed more extensively on silica gel to give 20.8 mg, 40%, of pure title compound.

EXAMPLE 41

[2R-(2beta,4beta,6alpha,7beta)]-7-[[(2,6-Dimethoxyphenyl)carbonyl]amio]-4-methyl-8-oxo-5-thia-1-azatricyclo[4.2.0.0/2,4/]octane-2-carboxylic acid monosodium salt A heterogenous solution of 97.9 mg, 0.19 mmol of [2R-(2β,4β,6α,7β)]-7-[[2,6-dimethoxyphenyl)carbonyl]amino]-4-methyl-8-oxo-5-thia-1-azatricyclo[4.2.0/2,4-/]octane-2-carboxylic acid (4-nitrophenyl)methyl ester and 97.6 of Palladium on Carbon in 2.0 mL of ethyl acetate and 24.0 mg, 0.286 mmol, 1.5 equivalets of Sodium bicarbonate in 2.0 mL of H$_2$O was hydrogenated at circa one atmosphere for 2 hrs. and 5 min. The solution was filtered through a pad of Celite and the pad washed with 1.0 mL portions of both ethyl acetate and water. The aqueous phase was chromatographed on a C-18 reverse phase HPLC using a gradient of 0% to 50% acetonitrile water in 25 min. The appropriate fractions were combined and lyophilized to give 12.2 mg, 16% of pure title compound.

EXAMPLE 42

[2R-(2beta,4beta,6alpha,7beta)]-4-Methyl-8-oxo-7-[[(4pyridinylthio)acetyl]amino]-5-thia-1-azatricyclo[4.2.0.0/2,4/]octane-2-carboxylic acid (4-nitrophenyl)methyl ester A solution of 0.205 mmol of p-nitrobenzyl 5R-6β-amino-2-methyl-(2,3)-α-methylene-penam-3-carboxylate in 2.0 mL dry chloroform, was diluted with 20 mL of dry methylene chloride, treated with 92 μL, 0.660 mmol, 2.98 equivalents of triethylamine and with 77.8 mg, 0.347 mmol, 1.57 equivalents of the acid chloride hydrochloride 4-(pyridylthio)acetyl chloride hydrochloride. The reaction was stirred 30 minutes, and washed two times with 10 mL each of saturated Sodium bicarbonate, dried with Magnesium sulfate, filtered and concentrated to dryness on a rotary evaporator to give 159.2 mg.

All the above was dissolved in ethyl acetate/hexanes (8:2) and chromatographed on silica gel. The appropriate fractions were combined and concentrated to dryness on a rotary evaporator to give 26.1 mg, 25% of the title compound.

EXAMPLE 43

[2R-(2beta,4beta,6alpha,7beta)]-4-Methyl-8-oxo-7-[[(4-pyridinylthio)acetyl]amino]-5-thia-1-azatricyclo [4.2.0.0/2,4/]octane-2-carboxylic acid monosodium salt A solution of 64.6 mg, 0.129 mmol, of [2R-(2β,4β,6α,7β)]-4-methyl-8-oxo-7-[[(4-pyridinylthio)acetyl]amino]-5-thia-1-azatribicyclo [4.2.0.0/2,4/]octane-2-carboxylic acid (4-nitrophenyl)methyl ester in 3.5 mL of ethyl acetate was added to a solution of 16.3 mg, 0.194 mmole, 1.50 equivalents of Sodium bicarbonate in 1.0 mL of water. The heterogenous solution was treated with 61.7 mg of 10% Palladium on Carbon and hydrogenated at 1 atmosphere for 4¾ hours. The reaction was filtered through a Celite pad and the pad was washed with small volumes of both ethyl acetate and water.

The aqueous phase was chromatographed on C-18 reverse phase HPLC using a gradient of 0% to 50% acetonitrile/water in 25 min. The appropriate fractions were combined and lyophilized to give 7.5 mg, 15%, of the title compound.

EXAMPLE 44

[2R-(2beta,4beta,5beta,6alpha,7beta)]-4-Methyl-8-oxo-7-[(phenylacetyl)amino]-5-thia-1-azatricyclo-[4.2.0.0/2,4/]octane-2-carboxylic acid 5-oxide (4-nitrophenyl)methyl ester A solution of 50.0 mg, 0.106 mmole, of 2R-(2β,4β,6α,7α)]-7-methoxy-4-methyl-5-oxo-7-[(phenylacetyl)amino]-5-thia-1-azatricyclo[4.2.0.0/2,4-/]octane-2-carboxylic acid (4-nitrobenzyl)methyl ester in 3.0 mL of methylene chloride was cooled in an ice-water bath and treated with 22.7 mg, 0.131 mmole, 1.23 equivalent of meta-chloroperoxybenzoic acid. The reaction was stirred 80 min. and treated with two additional portions of 4.2 and 4.8 mg of per acid, 15 mins. apart. After 10 minutes additional stirring, the solution was washed three times with 1.0 mL each of saturated Sodium bicarbonate and three times with 1.0 mL each of Sodium sulfite ($Na_2SO_3$). The solution was dried with Magnesium sulfate, filtered and concentrated on a rotary evaporator to give 50 mg.

All of the above material was dissolved in a small amount of ethyl acetate and chromatographed on silica gel. The appropriate fractions were combined and concentrated to dryness on a rotary evaporator to give 44.4 mg 85%, of the title compound.

EXAMPLE 45

[2R-(2beta,4beta,5beta,6alpha,7beta)]-4-Methyl-8-oxo-7-[(phenylacetyl)amino-5-thia-1-azatricyclo[4.2.0.0/2,4-/]octane-2-carboxylic acid 5-oxide sodium salt A soluton of 43.9 mg, 0.09 mmole, of [2R-(2β,4β,5β,6α,7β)]-4-methyl-8-oxo-7-[(phenylacetyl)amino]-5-thia-1-azatricyclo[4.2.0.0/2,4/]octane-2-carboxylic acid 5-oxide (4-nitrophenyl)methyl ester in circa 8 mL of methanol was treated with 42.1 mg of 10% Palladium on Carbon. The solution was hydrogenated for 1 hr 20 min. and filtered through Celite. The pad was washed with an additional 20 mL of methanol, and concentrated to dryness on a rotary evaporator. The residue was dissolved in a ca 5 mL of ethyl acetate and 2 mL of $H_2O$ and treated with 12.4 mg, 0.147 mmole, 1.62 equivalents of Sodium bicarbonate.

The aqueous phase was chromatographed on C-18 reverse phase HPLC using 0% to 30% acetonitrile/water in 30 min. By combining the appropriate fractions and lyophilization 11.7 mg, 34%, of the title compound was obtained.

What is claimed:

1. A compound of the formula

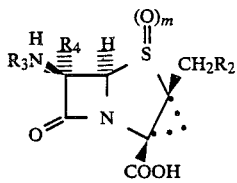

wherein $R_2$ is selected from the group consisting of hydrogen, lower alkyl, lower alkoxy, lower alkylthio, halo, hydroxy, cyano, trihalomethyl, azido, arylthio, five or six-membered heterocyclic thio, a five or six-membered heterocycle, and

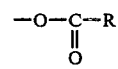

wherein R is hydrogen, lower alkyl, aryl, aryl substituted with substituents selected from the group consisting of halo and hydroxy or alkyl substituted with substituents selected from the group consisting of halo, trifluoromethyl, amino and cyano; $R_3$ is selected from the group consisting of hydrogen, an acyl group, a group of the formula

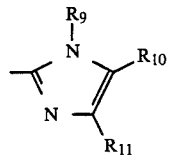

a group of the formula

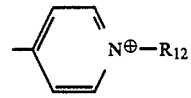

and a group of the formula

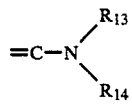

wherein another substituent is not present on the nitrogen at the 7-position; $R_4$ is selected from the group consisting of hydrogen, lower alkoxy, amino, lower alkylthio and amido; $R_{10}$ and $R_{11}$ are selected from the group consisting of hydrogen, halogen, cyano, hydroxy, carboxy, pyridyl, lower alkyl, aminoloweralkyl, hydroxyloweralkyl, $C_2$ to $C_6$ alkoxycarbonyl, lower alkyl, amino lower alkyl, dilower alkyl amino lower alkyl, phenyl and phenyl mono- or di-substituted with substituents selected from the group consisting of halo, lower alkyl, amino, nitro and trifluoromethyl; $R_9$ is selected from the group consisting of hydrogen, hydroxy, amino, lower alkyl, lower alkanoyl, lower alkoxy, lower alkanoylamino, lower alkyl amino, phenyl lower alkyl phenyl and phenyl mono- or di-substituted with substituents selected from the group consisting of halo, lower alkyl, amino, nitro and trifluoromethyl; $R_{12}$ is selected from the group consisting of lower alkyl, lower alkyl substituted with a substituent selected from the group consisting of halo, trifluoromethyl, amino and cyano and aralkyl; $R_{13}$ and $R_{14}$ are selected from the group consisting of lower alkyl, halo-lower alkyl, hydroxy-lower alkyl, lower alkoxy-lower alkyl, carbalkoxylower alkyl, cyano lower alkyl, carbonyl lower alkyl, alkyl, phenyl, phenyl mono- or di-substituted with substituents selected from the group consisting of halo, lower alkyl, amino, nitro and trifluoromethyl and cyclolower alkyl or $R_{13}$ and $R_{14}$ together with the nitrogen to which they are attached form a saturated heterocyclic ring having from 4 to 8 carbon atoms which may optionally contain one or two hetero atoms in place of a carbon atom and m is 0, 1 or 2 and the readily hydrolysable esters or salts of these compounds and hydrates of the compounds of formula I or of their esters or salts.

2. The compound of claim 1 wherein $R_3$ is selected from the group consisting of (a) 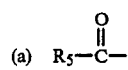

wherein $R^5$ is selected from the group consisting of alkyl, cycloalkyl, alkoxy, alkenyl, cycloalkenyl, cyclohexadienyl, or alkyl or alkenyl substituted with one or more halogen, cyano, nitro, amino, mercapto, alkylthio and cyanomethylthio groups;

(b) a substituent selected from the group consisting of

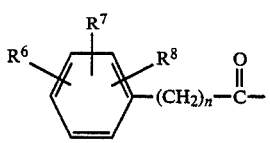

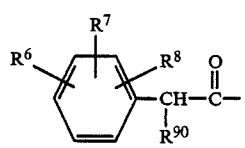

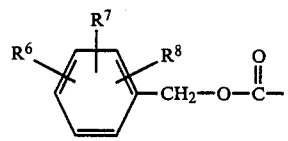

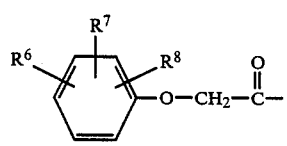

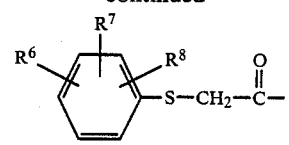

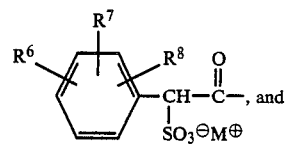

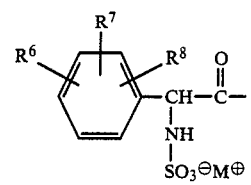

wherein n is 0, 1, 2 or 3; $R^6$, $R^7$, and $R^8$ is selected from the group consisting of hydrogen, halogen, hydroxyl, nitro, amino, cyano, trifluoromethyl, alkyl of 1 to 4 carbon atoms, and alkoxy of 1 to 4 carbon atoms or aminomethyl; and $R^{90}$ is selected from the group consisting of amino, hydroxyl, a carboxyl salt, protected carboxy and azido;

(c) a substituent group selected from the group consisting of

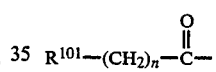

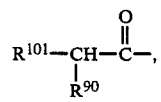

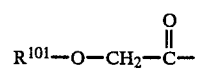

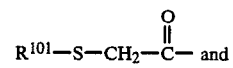

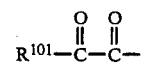

wherein n is 0, 1, 2 or 3; $R^{90}$ is as described above; and $R^{101}$ is a 5-, 6- or 7-membered heterocyclic ring containing 1, 2, 3 or 4 nitrogen, oxygen or sulfur atoms, which is unsubstituted or substituted with one or more halogen, hydroxyl, nitro, amino, cyano, trifluoromethyl, alkyl of 1 to 4 carbon atoms, or alkoxy of 1 to 4 carbon atoms (d) 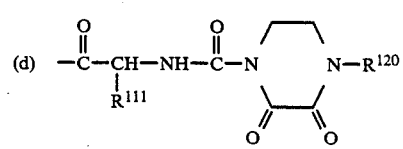

wherein $R^{111}$ is alkyl, hydroxyalkyl or an aromatic group of the formula

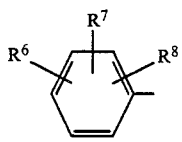

wherein R[6], R[7], and R[8] are as previously described, or a heteroaromatic as described for R[101] and R[120] is alkyl or alkyl substituted with one or more substituents selected from the group consisting of halo, cyano, nitro, amino and mercapto

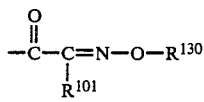 (e)

wherein R[101] is as described above and R[130] is hydrogen, lower alkyl and $C_3$-$C_7$ cycloalkyl or lower alkyl wherein the alkyl group is substituted with 1 or more halogen, cyano, nitro, amino, mercapto, lower alkylthio, aromatic of R[111], carboxyl, carboxylic salts, amido, lower alkoxycarbonyl, phenylmethoxycarbonyl, diphenylmethoxycarbonyl, hydroxyalkoxyphosphinyl, dihydroxyphosphinyl, hydroxy phenylmethoxy phosphinyl, or diloweralkoxyphosphinyl substituents;

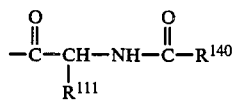 (f)

wherein R[111] is as described above and R[140] is

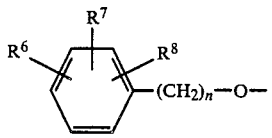

wherein R[6], R[7], R[8] and n are as described above, or R[140] is hydrogen, lower alkyl, amino, alkylamino, cyanoalkylamino, or acylamino; or lower alkyl substituted with halo, trifluoromethyl, amino or cyano

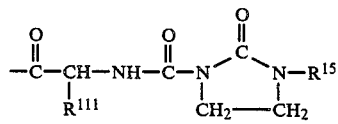 (g)

wherein R[111] is as described above and R[15] is hydrogen, alkylsulfonyl, —N═CH—R[111] wherein R[111] is as described above,

wherein R[16] is hydrogen, alkyl or halogen substituted alkyl, aromatic group as described by R[111] above, alkyl or alkyl substituted with one or more substituents selected from the group consisting of halogen, cyano, nitro, amino or mercapto.

3. The compound of claim 2 wherein R[3] is a carbocyclic aromatic group of the formula

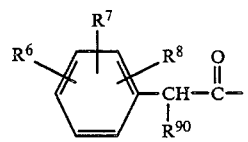

wherein R[90] is selected from the group consisting of amino, acylamino, hydroxyl, a carboxyl salt, benzyloxycarbonyl, formyloxy or azido; R[6], R[7] and R[8] is selected from the group consisting of hydrogen, halogen, hydroxyl, nitro, amino, cyano, trifluoromethyl, $C_1$-$C_4$ alkyl, $C_1$ to $C_4$ alkoxy and aminomethyl and R[2] is selected from the group consisting of hydrogen, lower alkyl, lower alkoxy, lower alkylthio, halo, hydroxy, cyano, trifluoromethyl, azido, arylthio, five or six-membered heterocyclic thio, a five or six-membered heterocycle, and

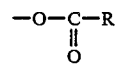

wherein R is hydrogen, lower alkyl, aryl, substituted aryl or substituted alkyl wherein said substituents on the aryl group are halo or hydroxy and the substituents on the alkyl group are halo, trifluoromethyl, amino or cyano.

4. The compound of claim 3 wherein R[6], R[7], R[8] are hydrogen and R[90] is hydrogen or hydroxy.

5. The compound of claim 4 wherein R[2] is hydrogen, lower alkyl or a five or six membered substituted mono or di- or unsubstituted heterocycle or heterocyclic thio wherein the substituents are selected from the group consisting of lower alkyl, oxo, hydroxy, lower alkoxy and carboxyl.

6. The compound of claim 5 wherein R[2] is hydrogen or lower alkyl.

7. The compound of claim 2 wherein the ester protecting group is in the form of the (4-nitrophenyl)-methylester.

8. A compound of claim 2 wherein R[3] is a group of the formula:

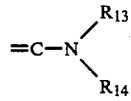

wherein R[13] and R[14] taken together with the nitrogen to which they are attached form a saturated heterocyclic ring having 4 to 8 carbon atoms and another substituent is not present on the nitrogen at the 7-position adjacent to the ring.

9. A compound of claim 1 wherein R[3] is an aliphatic group of the formula:

wherein R[5] is alkyl substituted by cyano.

10. A compound of claim 1 wherein R[3] is a group of the formula:

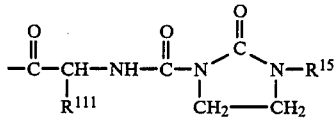

wherein $R^{111}$ is alkyl, hydroxy alkyl or an aromatic group of the formula:

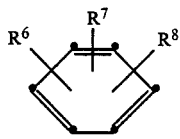

wherein $R^6$, $R^7$ and $R^8$ are selected from the group consisting of hydrogen, halogen, hydroxyl, nitro, amino, cyano, trifluoromethyl, $C_1$ to $C_4$ alkyl, $C_1$ to $C_4$ alkoxy and aminomethyl and $R^{15}$ is hydrogen, alkylsulfonyl, $-N=CH-R^{111}$,

(wherein $R^{16}$ is hydrogen, alkyl or halogen substituted alkyl), $R^{111}$, alkyl or substituted alkyl wherein the alkyl is substituted with one or more halogen, cyano, nitro, amino or mercapto groups.

11. A compound of claim 1 wherein $R_3$ is a group of the formula:

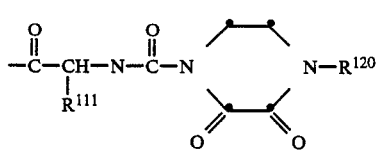

wherein $R^{111}$ is alkyl, hydroxyalkyl or an aromatic group of the formula:

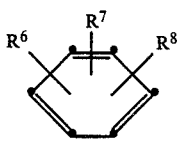

wherein $R^6$, $R^7$ and $R^8$ are selected from the group consisting of hydrogen, halogen, hydroxyl, nitro, amino, cyano, trifluoromethyl, $C_1$ to $C_4$ alkyl, $C_1$ to $C_4$ alkoxy, aminomethyl or a substituted 5-, 6- or 7-membered heterocyclic ring containing 1, 2, 3 or 4 nitrogen, oxygen or sulfur atoms and $R^{120}$ is alkyl or substituted alkyl wherein the alkyl group is substituted with one or more halogen, cyano, nitro, amino or mercapto groups.

12. A compound of claim 1 wherein $R_3$ is a group of the formula:

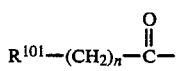

wherein $R^{101}$ is a substituted or unsubstituted 5-, 6- or 7-membered heterocyclic ring containing 1, 2, 3 or 4 nitrogen, oxygen or sulfur atoms and n is 0, 1, 2 or 3.

13. A compound of claim 1 wherein $R_3$ is a group of the formula:

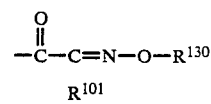

wherein $R^{101}$ is a unsubstituted or substituted 5-, 6- or 7-membered heterocyclic ring containing 1, 2, 3 or 4 nitrogen, oxygen or sulfur atoms wherein the heterocyclic ring is substituted by halogen, hydroxy, nitro, amino, cyano, trifluoromethyl, $C_1$ to $C_4$ alkyl or $C_1$ to $C_4$ alkoxy and $R^{130}$ is hydrogen, lower alkyl, $C_3$-$C_7$ cycloalkyl and substituted lower alkyl wherein the lower alkyl is substituted with one or more halogen, cyano, nitro, amino, mercapto, lower alkylthio, $R^{111}$, carboxyl, carboxylic salts, amido, lower alkoxycarbonyl, phenylmethoxycarbonyl, diphenylmethoxylcarbonyl, hydroxyalkoxyphosphinyl, dihydroxyphosphinyl, hydroxy(phenylmethoxy)phosphinyl or diloweralkoxyphosphinyl substituents.

14. The compound of claim 12 wherein $R_3$ taken with its attached nitrogen is 6β-(2-thienyl)acetamino-.

15. The compound of claim 13 wherein $R_3$ taken with its attached nitrogen is 6β-[2(2-amino-4-thiazolyl)-Z-2-(methoxyimino)-acetyl]amino-.

16. The compound of claim 13 wherein $R_3$ taken with its attached nitrogen is 6β-[2(2-amino-4-thiazolyl)-Z-2-(1-methyl-1-carboxy-ethoxyimino)-acetyl]amino-.

17. A compound of the formula

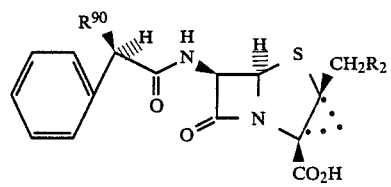

wherein $R^{90}$ is hydrogen or hydroxy and $R_2$ is hydrogen or lower alkyl and the readily hydrolysable esters or salts thereof or hydrates of said compound, its esters or salts.

18. The compound: [2R-(2α,4α,6β,7α)]-4-methyl8-oxo-7-[(phenylacetyl)amino]-5-thia-1 -azatricyclo[4.2.0.0²,⁴]octane-2-carboxyclic acid, sodium salt or the para-nitrobenzyl ester thereof.

19. The compound [2R-[2α,4α,6β,7α(R*)]]-7-[(phenylhydroxyacetyl)amino]-4-methyl-8-oxo-5-thia-1-azatricyclo[4.2.0.0/2,4/]octane-2-carboxylic acid, sodium salt or the para-nitrobenzylester thereof.

20. A compound of the formula

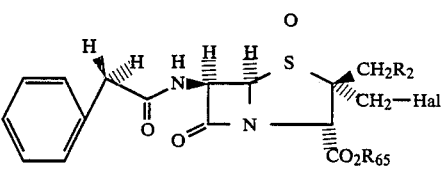

wherein $R_2$ is hydrogen or lower alkyl, Hal is halogen and $R_{65}$ is an ester protecting group.

21. The compound of claim 20 wherein wherein Hal is bromine and $R_2$ is hydrogen.

22. A compound of the formula

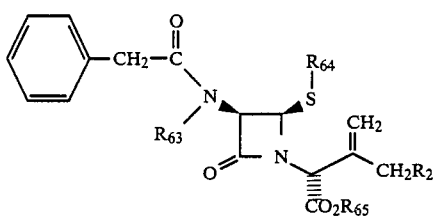

wherein R63 is trihalosubstituted acetyl, R64 is selected from the group consisting of halogen, Aryl NH—, Aryl S—, Alkyl S—, heterocyclicthio, Aryl O—, heterocyclicoxo, and the groups R—COS— and

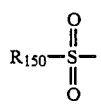

wherein R150 is alkyl or aryl, R65 is an ester protecting group and R2 is hydrogen or lower alkyl.

23. The compound of claim 22 wherein R64 is heterocyclicthio.

24. A compound of the formula

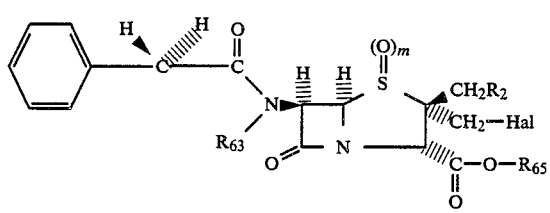

wherein m is 0, 1 or 2, R65 is an ester protecting group, R2 is hydrogen or lower alkyl, R63 is trihalosubstituted acetyl and Hal is halogen.

25. The compound of claim 24 wherein R2 is hydrogen and the trihalosubstituent is trifluoro.

26. The compound of claim 23 wherein R64 is heterocyclicthio of the formula

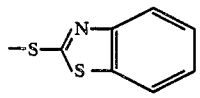

and R2 is hydrogen.

27. A compound of the formula:

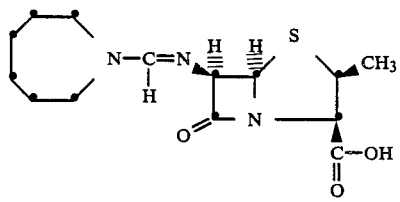

and the readily hydrolyzable esters or salts thereof and hydrates of the compound, its esters or salts.

28. The compound: [2R-(2β,4β,6α,7β]-7-[[hexahydro-1H-(azepin-1-yl)methylene]amino]-4-methyl-8-oxo-5-thia-1-azatricyclo[4.2.0.0$^{2,4}$]octane-2-carboxylic acid monosodium salt or the (4-nitrophenyl)methyl ester thereof.

29. A compound of the formula

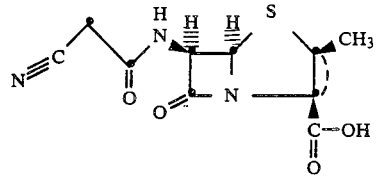

and the readily hydrolyzable esters or salts thereof and hydrates of the compound, its esters or salts.

30. The compound: [2R-(2β,4β,6α,7β)]-7 [(cyanoacetyl)amino]-4-methyl-8-oxo-5-thia-1-azatricyclo [4.2.0.0$^{2,4}$]octane-2-carboxylic acid or the (4-nitrophenyl) methyl ester thereof.

31. A compound of the formula:

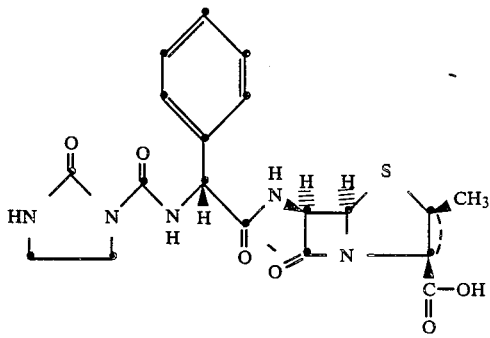

and the readily hydrolyzable esters or salts thereof and hydrates of the compound, its esters or salts.

32. A compound selected from the group consisting of: [2R-[2α,4α,6β,7α(R*)]]-4-methyl-8-oxo-7-[[[[(2-oxo-1-imidazolidinyl)carbonyl]amino]phenylacetyl]-amino]-5-thia-1-azatricyclo [4.2.0.0$^{2,4}$]octane-2-carboxylic acid and the (4-nitrophenyl)methyl ester thereof.

33. A compound of the formula

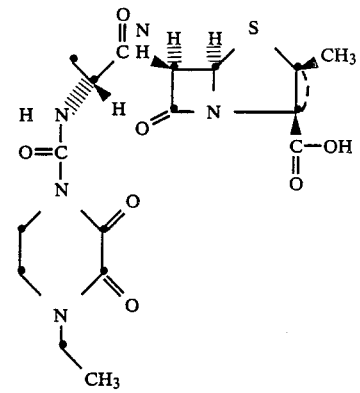

and the readily hydrolyzable esters or salts thereof and hydrates of the compound, its esters or salts.

34. A compound selected from the group consisting of: [2R-[2β,4β,6α,7β(R*)]]-7-[[[[(4-ethyl-2,3-dioxo-1-piperazinyl)carbonyl]amino]phenylacetyl]amino]-4-methyl-8-oxo-5-thia-1-azatricyclo [4.2.0.0$^{2,4}$]octane-2-carboxylic acid monosodium salt and the (4-nitrophenyl)methyl ester thereof.

35. A compound of the formula

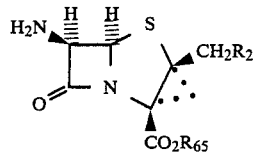

wherein $R_2$ is hydrogen or lower alkyl and $R_{65}$ is an ester protecting group or hydrogen.

36. The compound: [2R-(2α,4α,6β,7α)]-7-amino-4-methyl-8-oxo-5-thia-1-azatricyclo[4.2.0.0²,⁴]octane-2-carboxylic acid (4-nitrophenyl)methyl ester.

37. A compound of the formula

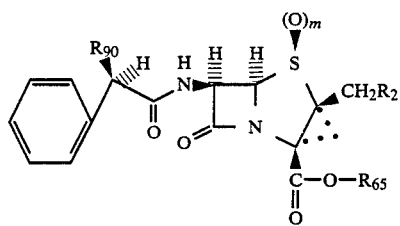

wherein $R_{65}$ is an ester protecting group or hydrogen, $R_2$ is hydrogen or lower alkyl, m is 0, 1 or 2 and $R^{90}$ is hydrogen or hydroxy.

38. The compound of claim 37 wherein $R_2$ is hydrogen and m is 1.

39. A compound of the formula

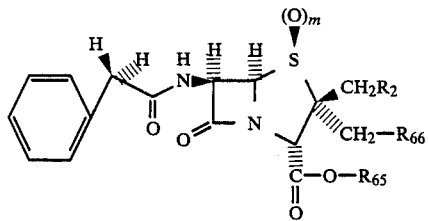

wherein m is 0, 1 or 2, $R_{65}$ is an ester protecting group or hydrogen, $R_2$ is hydrogen or lower alkyl and $R_{66}$ is halogen, mesylate, or tosylate.

40. The compound of claim 39 wherein $R_2$ is hydrogen and $R_{66}$ is halogen.

41. A compound in accordance with claim 40, [2S-(2α,3α,4β,5α,6β)]-3-bromomethyl-3-methyl-7-oxo-6-[(phenylacetyl)amino]-4-thia-1-azabicyclo[3.2.0]heptane-2-carboxylic acid (4-nitrophenyl)methyl ester 4-oxide.

42. A compound in accordance with claim 40, [2S-(2α,3α,5α,6β)]-3-(bromomethyl)-3-methyl-7-oxo-6-[(phenylacetyl)amino]-4-thia-1-azabicyclo[3.2.0]heptane-2-carboxylic acid (4-nitrophenyl)methyl ester.

43. A compound of the formula

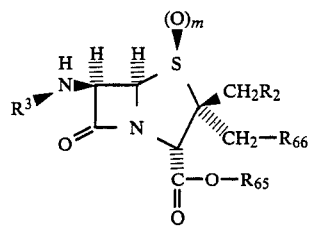

wherein m is 0, 1 or 2, $R_2$ is hydrogen or lower alkyl, $R_{65}$ is an ester protecting group, or hydrogen, or lower alkyl, $R_{66}$ is a leaving group, and $R_3$ is a protecting group selected from the group consisting of hydrogen, an acyl group, a group of the formula

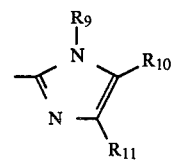

a group of the formula

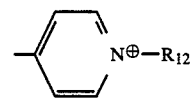

and a group of the formula

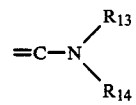

wherein another substituent is not present on the nitrogen atom at the 7-position;
$R_{10}$ and $R_{11}$ are selected from the group consisting of hydrogen, halogen, cyano, hydroxy, carboxy, pyridyl, lower alkyl, aminoloweralkyl, hydroxylower alkyl, $C_2$ to $C_6$ alkoxycarbonyl, lower alkyl amino lower alkyl, dilower alkyl amino lower alkyl, phenyl and phenyl mono- or di-substituted with substituents selected from the group consisting of halo, lower alkyl, amino, nitro and trifluoromethyl; $R_9$ is selected from the group consisting of hydrogen, hydroxy, amino, lower alkyl, lower alkanoyl, lower alkoxy, lower alkanoylamino, loweralkylamino, phenyl lower alkyl phenyl and phenyl mono- or di-substituted with substituents selected from the group consisting of halo, lower alkyl, amino, nitro and trifluoromethyl; $R_{12}$ is selected from the group consisting of lower alkyl, lower alkyl substituted with a substituent selected from the group consisting of halo, trifluoromethyl, amino and cyano and aralkyl; $R_{13}$ and $R_{14}$ are selected from the group consisting of lower alkyl, halo-lower alkyl, hydroxy-lower alkyl, lower alkoxy-lower alkyl, carbalkoxyloweralkyl, cyanoloweralkyl, carbonyl lower alkyl allyl, phenyl, phenyl mono- or di-substituted with substituents selected from the group consisting of halo, lower alkyl, amino, nitro and trifluoromethyl and cyclolower alkyl or $R_{13}$ and $R_{14}$ together with the nitrogen to which they are attached form a heterocyclic ring having from 4 to 8 atoms which may optionally contain one or two other hetero atoms in place of a carbon atom and m is 0, 1 or 2 and the readily hydrolysable esters or salts of these compounds and hydrates of the compounds or of their esters or salts.

* * * * *